(12) United States Patent
Nozaki et al.

(10) Patent No.: US 7,127,354 B1
(45) Date of Patent: Oct. 24, 2006

(54) METHOD OF DISPLAYING GENE DATA, AND RECORDING MEDIUM

(75) Inventors: Yasuyuki Nozaki, Kanagawa (JP); Ryo Nakashige, Kanagawa (JP); Takuro Tamura, Kanagawa (JP)

(73) Assignee: Hitachi Software Engineering Co., Ltd., Kanagawa (JP)

( * ) Notice: Subject to any disclaimer, the term of this patent is extended or adjusted under 35 U.S.C. 154(b) by 194 days.

(21) Appl. No.: 10/129,251

(22) PCT Filed: Sep. 19, 2000

(86) PCT No.: PCT/JP00/06385

§ 371 (c)(1),
(2), (4) Date: Apr. 30, 2002

(87) PCT Pub. No.: WO02/25489

PCT Pub. Date: Mar. 28, 2002

(51) Int. Cl.
*G01N 33/48* (2006.01)
(52) U.S. Cl. .......................................... 702/19; 702/27
(58) Field of Classification Search ................. 435/6; 702/19, 27
See application file for complete search history.

(56) References Cited

U.S. PATENT DOCUMENTS 5,598,350 A    1/1997   Kawanishi et al. ......... 364/496

FOREIGN PATENT DOCUMENTS

JP      07-274965      11/1994

OTHER PUBLICATIONS

Eisen et al., Proc. Natl. Acad. Sci., vol. 95, pp. 14863-14868, 1998.*
Webster's II New Riverside University Dictionary, The Riverside Publishing Company, 1984, p. 330.*
Webb et al., PNAS, vol. 97, pp. 5773-5778, May 2000.*
DeRisi et al., Science, vol. 278, pp. 680-686, 1997/.*
Ross, Douglas T., et al., Systematic variation in gene expression patterns in human cancer cell lines, Nature Genetics, vol. 24, pp. 227-235 (Mar. 2000).
Samuel F. Schluter et al., "Molecular Origins and Evolution of Immunoglobulin Heavy-Chain Genes of Jawed Vertebrates", Immunology Today (Nov. 1997), vol. 18, No. 11, pp. 543-549.
Wolfgang Ludwig et al., "A Software Environment for Sequence Data", Technische Universitat, Munich, 43 pages, 1997.
Olivier Lichtarge et al., "Identification of Functional Surfaces of the Zinc Binding Domains of Intracellular Receptors", J. Mol. Biol. (1997), vol. 274, pp. 325-337.

* cited by examiner

*Primary Examiner*—Tim Vo
*Assistant Examiner*—Cheyne D. Ly
(74) *Attorney, Agent, or Firm*—Reed Smith LLP; Stanley P. Fisher, Esq.; Juan Carlos A. Marquez, Esq.

(57) ABSTRACT

A method of displaying gene data assists in discovering expression patterns specific to gene functions and inferring the function of a gene of which the function is unknown. A threshold value representing the degree of similarity of expression patterns is established in advance, and genes having the same function and genes with similar expression patterns to them are extracted and displayed. Cluster analysis is performed on the extracted genes by re-selecting the experiment patterns for clustering. Calculations are performed to see how many functions the genes belonging to a subtree have, and the proportion of each function in the subtree is determined. If a proportion exceeds a predetermined threshold value, they are regarded as a cluster (collection of genes with similar functions) and extracted.

1 Claim, 23 Drawing Sheets

200

300

STRUCTURE SEQUENCE gene[i] (i = 1,2,...,m)

| MEMBER NAME | | VALUE |
|---|---|---|
| 600 — GENE ID | | 23 |
| 601 — ATTRIBUTES | 603 — GENE NAME | PHOSPHOGLYCERATE MUTASE |
| | ORF | YDL021W |
| | 604 — FUNCTION | GLYCOLYSIS |
| 602 — EXPRESSION DATA | 605 — EXPERIMENT1 | 12.3 |
| | EXPERIMENT2 | 29.0 |
| | EXPERIMENT3 | 18.5 |
| | EXPERIMENT4 | 9.6 |
| | ⋮ | ⋮ |
| | EXPERIMENT n | 29.4 | n- DIMENSIONAL VECTOR DATA results[i] (i =1,2,...,func_num)

|  | MEMBER NAME | VALUE |
|---|---|---|
| 2200 | threshold rate | 0.75 |
| 2201 | threshold leaf | 10 |
| 2202 | result | 8, 38, ... |

METHOD OF DISPLAYING GENE DATA, AND RECORDING MEDIUM

This application is the National Phase of International Application PCT/JP00/06385 filed Sep. 19, 2000 which designated the U.S. and that International Application was not published under PCT Article 21(2) in English.

TECHNICAL FIELD

The present invention relates to a method of displaying gene expression data obtained as a result of hybridisation with a specified gene in a manner that is visually easy to understand and which allows the function and role of the gene to be easily conjectured.

BACKGROUND ART

As genome sequences are determined for an increasing variety of species, a great deal of attention is being paid to a so-called genome comparison method aimed at discovering new information from genetic differences between them. The genome comparison method aims to find out genes responsible for the development of individual species, in order to look for groups of genes which are believed to be common to all living organisms, or, conversely, estimate characteristics specific to individual species.

Recent years have witnessed the development of an infrastructure in the form of DNA chips and DNA microarrays (hereinafter referred to as 'biochips'. As a result, the interests of molecular biologists are turning from inter-species data to intra-species data, in other words, they are focusing on the analysis of genes expressed simultaneously in a particular cell. Thus, there is an increasing number of ways in which data is extracted and used, alongside the more conventional comparisons between species.

For instance, if a previously unknown gene is discovered and found to exhibit the same expression pattern as a known gene, it may be inferred to have a similar function to that of the known gene. The functional significance of such genes and the proteins themselves are being studied in the form of functional units and groups. Meanwhile, as far as interactions between them are concerned, the direct and indirect effect of a given gene is being analysed by comparison with known enzyme reaction data or metabolic data, or more directly by destroying the gene or causing it to overreact, thus eliminating the expression thereof or expressing it in quantity to study the expression patterns of all genes. An example of success in this field is provided by an expression analysis of yeast performed by a group led by P. Brown of Stanford University in the USA (Michael B. Eisen et al.; Cluster analysis and display of genome-wide expression patterns. Proc. Natl. Acad. Sci. 95 (25); 14863–8, 8 Dec. 1998). This group used DNA microarrays to hybridise genes extracted from cells in a time series, representing the degree of gene expression (intensity of hybridised fluorescent signals) numerically. By allocating colours to the numerical values they then displayed the expression processes of the individual genes in a manner which was easy to understand. They then clustered genes with similar expression pattern processes in a cycle of cells (those with similar degrees of expression at a given point in time).

FIG. 27 is an example of how the result of a standard cluster analysis of gene expression is displayed according to this method. The experiment cases are displayed in the horizontal direction, and the genes arranged in the vertical direction. The degree of expression of each gene in each experiment case is denoted by the density of colour. Denser colours represent higher degrees of expression. A dendrogram is displayed on the left of the drawing. The dendrogram shows how in the process of clustering two closest clusters have been merged in each case, while the length of each branch corresponds to the relative distance between two clusters on merging.

FIG. 28 is an example of another display representing the similarity of gene expression patterns. Observed data on individual genes is arranged on the right, while the dendrogram displayed on the left has been prepared on the basis of these gene expression patterns.

With developments in biology the functions of genes are gradually being clarified, and biologists are attempting to analyse them by combining expression data and known information. Analysis by dendrogram allows biologists to look for biologically meaningful clusters (groups of genes). In other words, if the expression patterns of individual genes in a cluster are similar and there are many of known function with the same pattern, this is extracted as a meaningful cluster. Such clusters are herein referred to as function clusters. Vertical bars 2801 and 2802 in FIG. 28 are examples of such function clusters. For instance, if there is a gene of unknown function within a function cluster, it is possible to infer that it possesses a similar function to those in the same cluster with a known function. What is more, by examining the expression pattern of a function cluster it is possible to discover the expression process specific to the function.

A huge amount of gene data needs to be handled in the actual analysis of gene expression patterns. This is because biochips make it possible to observe genes of the order of between several thousand and several tens of thousands at the same time. With developments in biochip technology the number of genes which it is possible to observe simultaneously is set to increase by leaps and bounds, lending powerful support to the process of clarifying the mechanism of life.

As the number of such genes increases in this manner, it becomes extremely difficult to comprehend the workings of all of them. A dendrogram will contain thousands or tens of thousands of genes, and even the subtrees illustrated in FIGS. 27 and 28 will be very complex and include many fine branches, making it difficult to decide what sort of classification has been carried out.

Researchers will have to spend much time and effort choosing function clusters for these dendrograms. Some commercially available gene expression clustering tools have display functions for dendrograms and gene names, but none gives any suggestion as to what clusters merit attention.

In view of the above problems with conventional technology, it is a first object of the present invention to take the results of clustering, extract from them groups of genes having the same function and genes having similar expression patterns to the groups of genes, and provide a function and display for re-analysing these genes. This makes it possible to assist in discovering specific expression patterns for gene functions, surmise unknown gene functions, and infer whether or not genes known to have one function have other functions as well.

It is a second object of the present invention to provide a means of automatically sorting clusters of genes having similar expression patterns and the same function, and displaying them in a form in which it is easy for researchers to understand their characteristics.

DISCLOSURE OF THE INVENTION

In order to achieve the first object, the method of displaying gene data to which the present invention pertains comprises the steps of displaying a plurality of gene expression patterns and a dendrogram obtained by cluster analysis of those expression patterns in such a manner as to correspond to each other; specifying the function of a particular gene and the distance thereof on the dendrogram; and highlighting that subtree in the dendrogram which contains the gene with the specified function and which has, as a root, a node whose distance from the gene on the dendrogram is less than the specified distance.

This method of displaying gene data does so in a form which facilitates the visual appreciation of a plurality of gene expression pattern data and permits easy conjecture of the function and role of a gene. It achieves this by first clustering according to gene expression data, and, on a dendrogram showing the results, highlighting the branches which correspond to gene groups having the same functions and those exhibiting similar expression patterns to them, thus allowing the user to comprehend the position of these genes in the dendrogram as a whole.

The distance from a gene on the dendrogram may be specified by drawing a straight line crossing branches of the dendrogram.

This method of displaying gene data may further comprise the step of extracting and displaying only the highlighted subtree and the expression pattern of a gene corresponding to the highlighted subtree.

The method may further comprise the step of performing cluster analysis on the extracted expression patterns.

Moreover, the method may further comprise the steps of specifying a range within which to perform cluster analysis on the extracted expression patterns, and performing cluster analysis on the expression patterns within the specified range.

In order to achieve the second object, a method of displaying gene data to which the present invention pertains comprises the steps of displaying a dendrogram obtained by performing cluster analysis on a plurality of gene expression patterns; specifying the function of genes to be cluster-extracted and a condition for cluster extraction; and highlighting gene clusters which satisfy the conditions in units of subtree of the dendrogram.

This method of displaying gene data does so in a form which facilitates the visual appreciation of a plurality of gene expression pattern data and permits easy conjecture of the function and role of a gene. It is capable of automatically extracting and displaying clusters where large numbers of genes exhibiting similar expression patterns and having known functions are gathered.

The condition for extracting clusters may comprise a minimum proportion of genes having the specified function within the subtree, and a minimum number of genes in one cluster that have the specified function.

Moreover, in order to achieve the second object, a method of displaying gene data to which the present invention pertains comprises the steps of displaying a dendrogram obtained by performing cluster analysis on a plurality of gene expression patterns; selecting a subtree from the dendrogram; and displaying proportions of genes contained within the selected subtree by function.

Selecting a subtree from the dendrogram obtained by performing cluster analysis and displaying it in detail allows the user to understand what sort of gene functions are gathered there, and helps infer unknown gene functions.

Furthermore, in order to achieve the second object, a method of displaying gene data to which the present invention pertains may comprise the steps of displaying a dendrogram obtained by performing cluster analysis on a plurality of gene expression patterns; selecting a subtree from the dendrogram; and displaying on a graph an average expression pattern of the selected subtree.

Selecting a subtree from the dendrogram obtained by performing cluster analysis and displaying expression patterns in detail allow the user to understand what sort of expression patterns are specific to functions. It is also possible to display variance alongside average expression values.

The recording medium capable of being read by a computer to which the present invention pertains is such that a computer program for implementing a plurality of steps according to any of the above methods is recorded thereon.

BEST MODE FOR CARRYING OUT THE INVENTION

There follows, with reference to the appended drawings, a more detailed description of the present invention.

First Embodiment

To begin with, there follows a description of an embodiment aimed at achieving the first object of the present invention.

Figure 1:
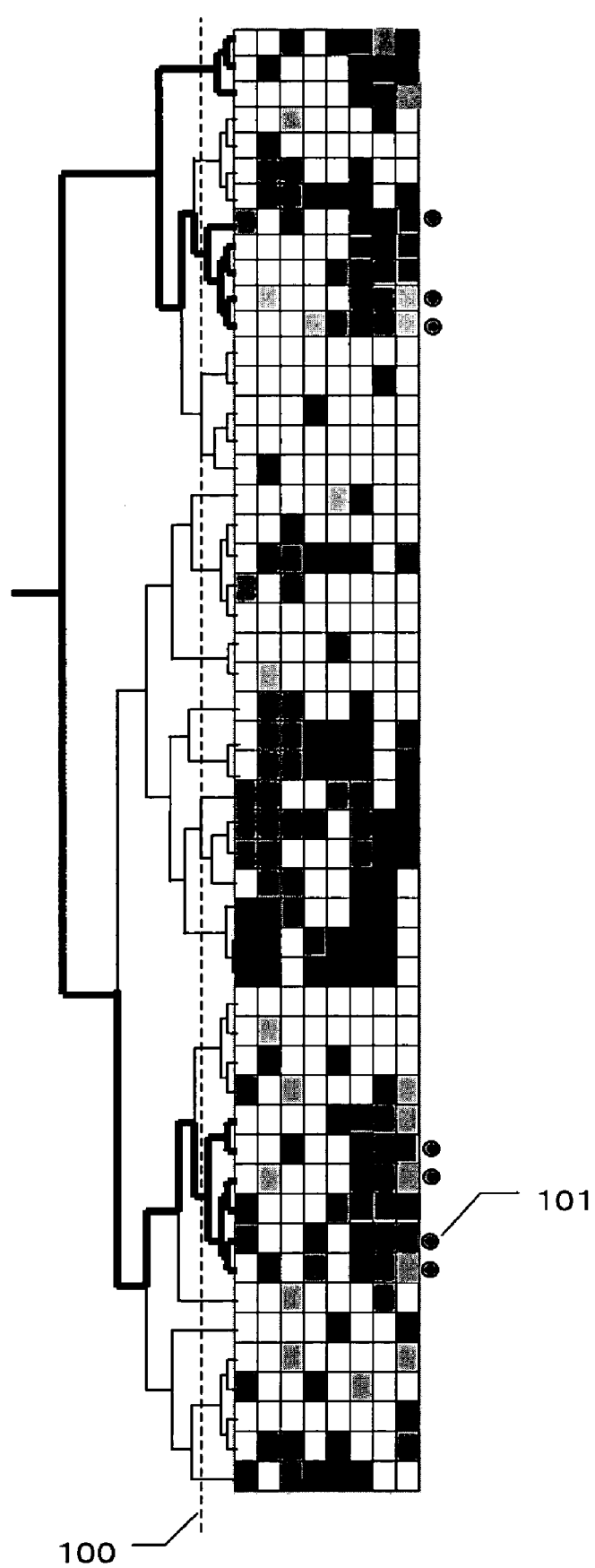
FIG. 1 illustrates an example of a screen display according to the present invention (screen display wherein genes having the same function and genes with similar expression patterns to them are highlighted)

FIG. 1 illustrates an example of a screen display aimed at achieving the first object of the present invention, where genes having the same function and genes with similar expression patterns to them are highlighted. If the user selects one function of a gene, the system searches the dendrogram for genes having that function and genes with similar expression patterns to them, and highlights them. Genes having the selected function are those with a mark numbered 101. Genes without this mark have different or unknown functions.

By similar expression pattern is meant that the distance between the clusters is small, which is to say the branch on the dendrogram is short. A threshold value is placed on the distance, and genes in a subtree whose distance is less than the threshold value are regarded as having similar expression patterns. In the dendrogram illustrated in FIG. 1, the vertical broken line 100 represents the threshold value and crosses several (more than two) branches of the dendrogram. In the example illustrated, genes which share the same subtree from this line 100 as far as the leaves are regarded as having similar expression patterns, and the relevant branches of the tree pattern are highlighted.

By highlighting effectively those groups of genes which have the same function and genes with similar expression patterns to them, this method of display makes it possible to see at a glance what positions they occupy on the dendrogram as a whole. Gene groups of this sort will be referred to as functionally related genes.

Figure 2:
FIG. 2 illustrates an example of a screen display according to the present invention (screen display wherein only genes having the same function and those with similar expression patterns to them have been extracted and displayed)

FIG. 2 is a screen display in which only the genes highlighted in FIG. 1 are displayed. In other words, only those genes having the same function and those with similar expression patterns to them are extracted and displayed. As shown in FIG. 2, gathering functionally related genes which have hitherto been dispersed over a dendrogram together for display allows users to infer the expression pattern specific to a function. In the display example illustrated in FIG. 2 there is an expression pattern common to each gene in the range 200 of part of the experiment case (horizontal axis), and it can be inferred that this range 200 may comprise a pattern specific to a function.

Figure 3:
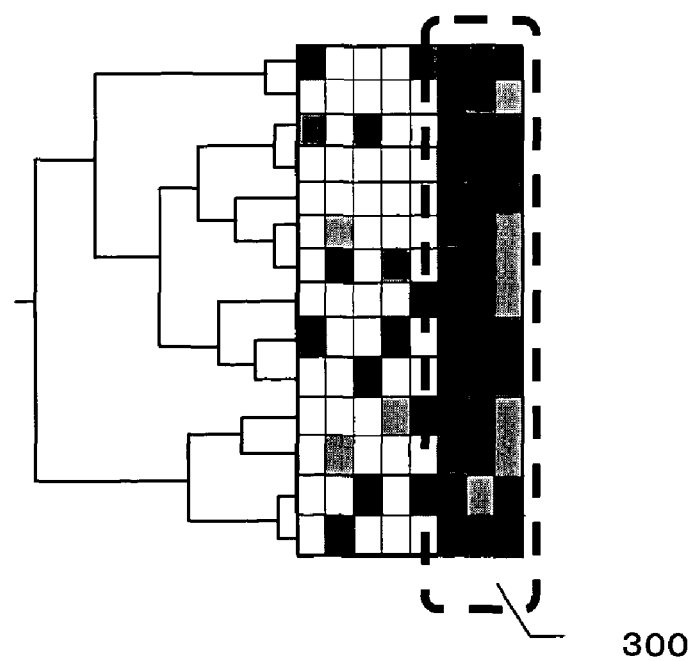
FIG. 3 illustrates an example of a screen display according to the present invention (screen display when a different method of clustering has been applied to the data in FIG. 2)
Figure 4:
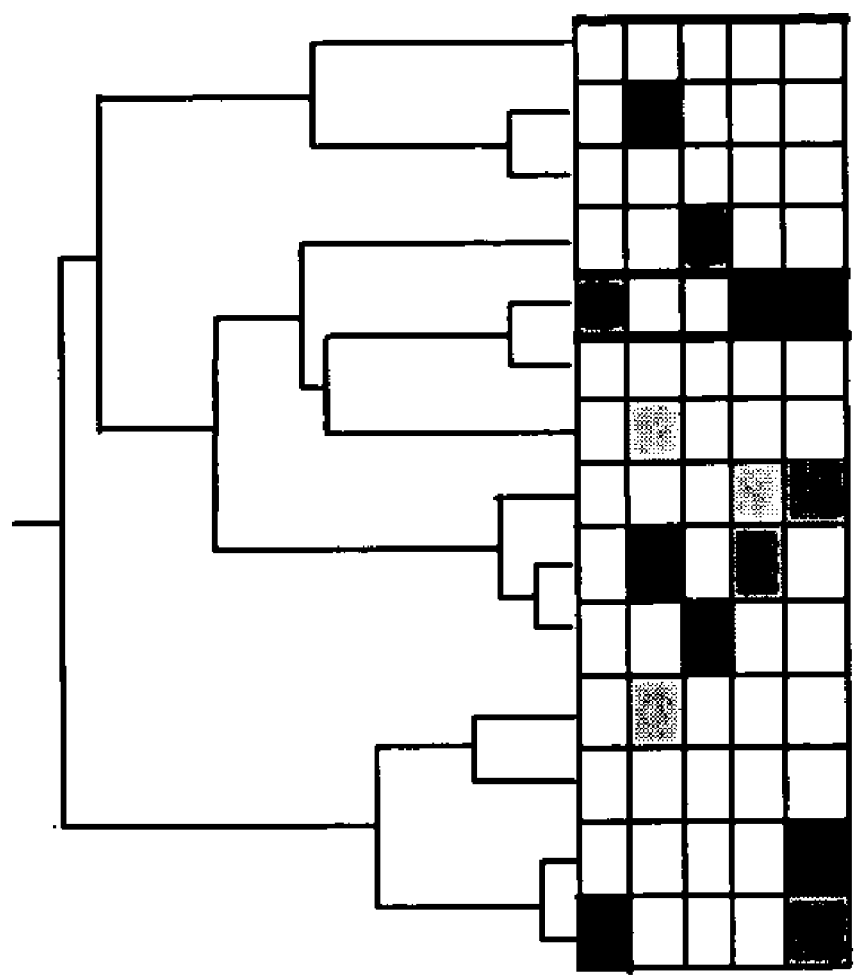
FIG. 4 illustrates an example of a screen display according to the present invention (screen display when further clustering has been applied to the data in FIG. 3 after removing a similar expression pattern region)

FIG. 3 illustrates an example of a screen display when a different method of clustering has been applied to the data in FIG. 2. Meanwhile, FIG. 4 illustrates an example of a screen display when, after removing from FIG. 3 the expression pattern (300) inferred to be specific to the function, further clustering has been applied to the remaining data. By reanalysing functionally related genes in this manner it is possible to help surmise unknown gene functions, and infer whether or not the genes have other functions.

Figures 5, 6:
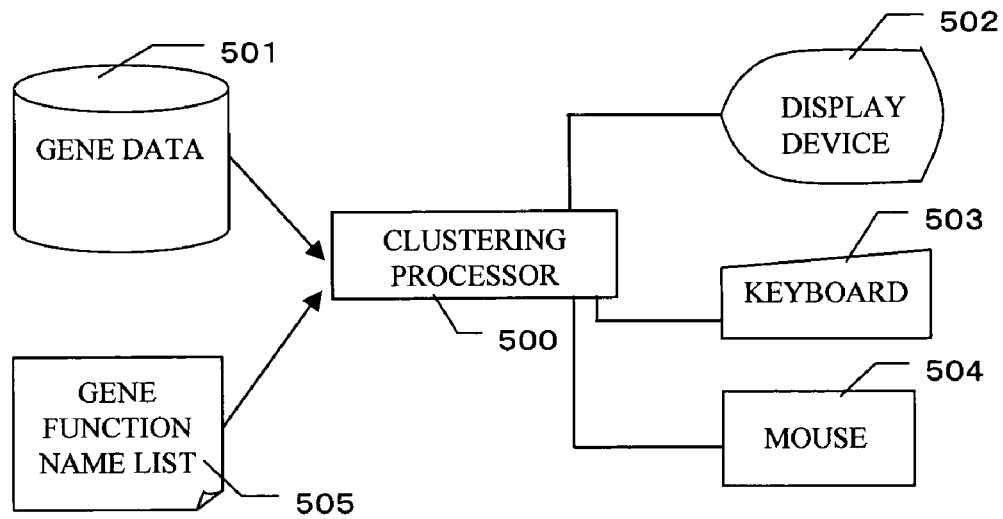
FIG. 5 is a system configuration diagram of the present invention.
FIG. 6 illustrates an example of gene data.

FIG. 5 is a system configuration diagram of the present invention. This system comprises gene data 501 which records gene information and expression processes, a clustering processor 500 which performs clustering in accordance with the gene expression processes and analyses it in order to display it in the form of a dendrogram, a display device 502 for displaying the dendrogram, a keyboard 503 and mouse 504 for inputting values into the system and operating selections, and a gene function name list 505 which is used for automatically extracting function clusters. The clustering processor 500 comprises a computer and its program. The program can be recorded on a CD-ROM or other recording medium, and is loaded by being read by the computer. Alternatively it may be downloaded from another computer by way of a network. The gene data may be obtained from a database which is managed by a server computer located at a distance, instead of using the data stored in the memory device 501.

FIG. 6 illustrates the detailed structure of the gene data 501. Gene information is stored in a sequence of an m number of elements called gene[i] (i=1, 2, . . . m), where m is the number of genes included in the gene data. Gene data comprises gene ID (600) which uniquely identifies the gene, attribute information (601) which represents the gene, and expression data (602) obtained from a DNA chip, DNA micorarray or other biochip. Attributes representing the gene include, e.g., gene name (603), ORF (604) and gene function (605). Other gene attributes may be defined as members of a gene information structure. In expression data (602), there is stored numerical data on the degree of expression of the gene in each experiment (intensity of fluorescent signals after hybridisation reaction). In the present embodiment, the number of experiments is n, and expression data for one gene is treated as an n-dimensional vector.

Figure 7:
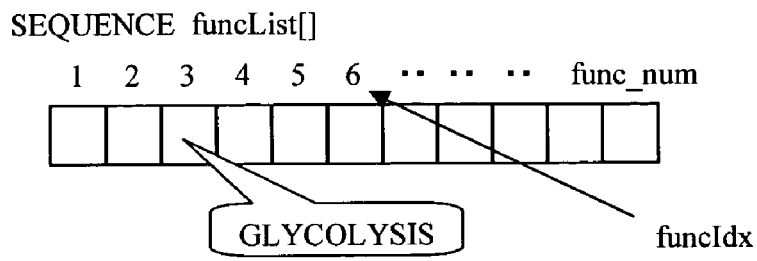
FIG. 7 illustrates an example of a gene function name list.

FIG. 7 illustrates the concrete structure of the gene function name list (505). The gene function name list is represented by a sequence funcList[ ] comprising a number func_num of elements. Names of functions are contained within the sequence. The index of the sequence funcList[ ] is represented as funcIdx, and is treated as an ID corresponding to the function. Genes with unknown functions are also recorded in the funcList[ ] with, for instance, the function name 'UNKNOWN'.

Figure 8:
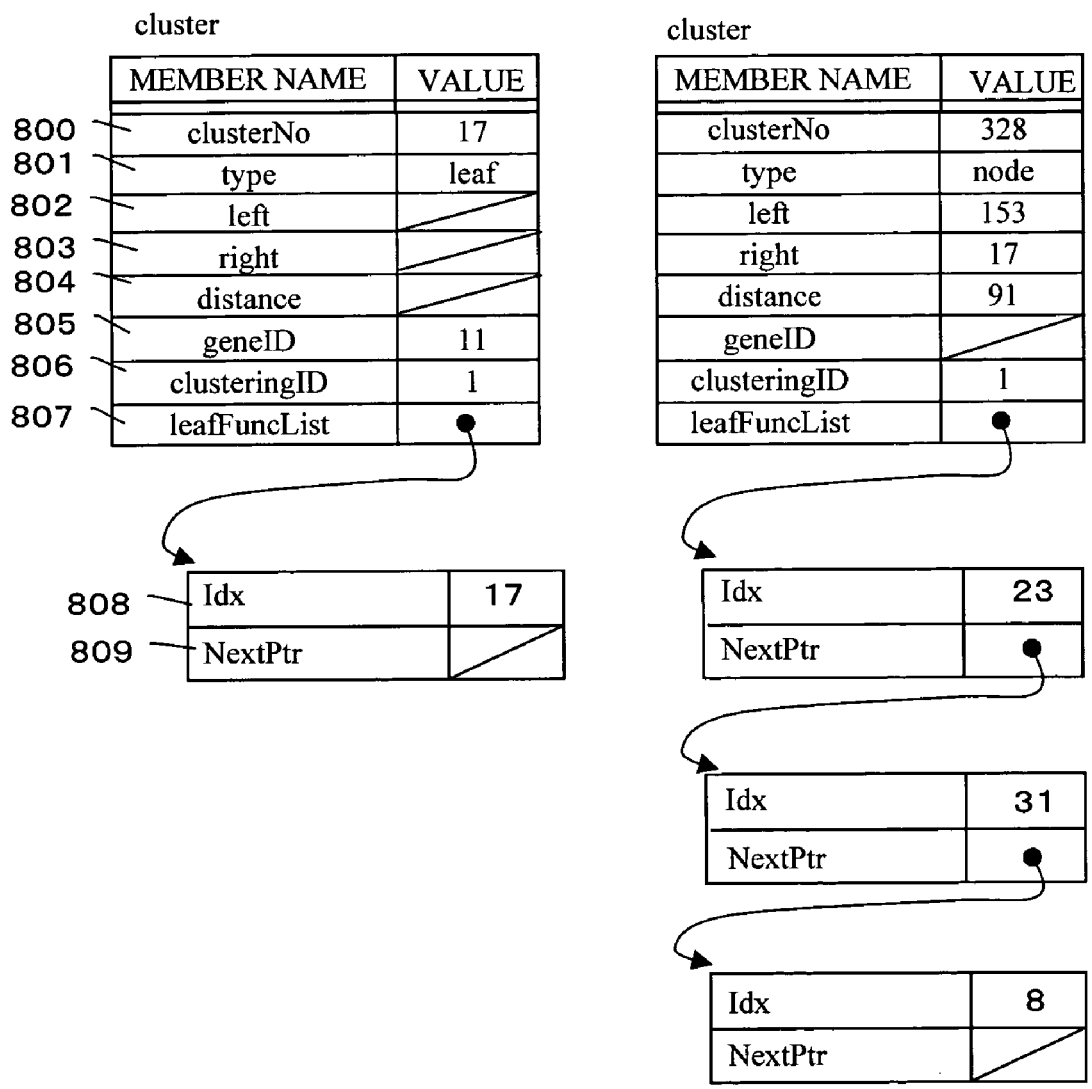
FIG. 8 illustrates an example of a cluster structure.

FIG. 8 illustrates an example of a cluster structure used in clustering. Each cluster structure corresponds to a node or leaf of the dendrogram. In order to identify the individual clusters, each cluster structure is uniquely represented by the pair of a clusterNo (800) and a clusteringID (806). The clusteringID (806) is an ID uniquely determined for each method of clustering, while the clusterNo (800) is used as an ID to represent the node in one clusteringID.

There are two types of cluster structure, i.e., one for leaf (left) and another for node (right), corresponding to clusters representing leaves and those representing medial nodes respectively, denoted by the value of the type member (801). The node-type cluster structures are generated successively in merge processing during clustering. Two clusters prior to merging can be traced from the left (802) and right (803) values, and the distance ((dis)similarity) between them is retained as the distance (804) value. The clusterNo (800) is included in the left and right values. The leaf type cluster structures, on the other hand, each correspond to one gene, and gene information structure data can be referred to by storing GENE ID (600) in geneID (805).

In the case of node type cluster structures, the functions of the genes corresponding to leaf type clusters which belong to clusters are stored by type in the leafFuncList (807) in a list structure. In the case of leaf type cluster structures, the functions of corresponding genes are stored in leafFuncList (807) in a list structure. One list comprises an idx (808) for storing the function ID, and a NextPtr (809) for storing a pointer to the next list. The function ID which goes in idx is the index of the funcList in the gene function name list. If a gene has a plurality of functions, these are added in the leafFuncList. For instance, if a gene has the functions 'TRANSPORT', 'TCA CYCLE' and 'GLYCOLYSIS', the funcList comprises three lists.

Figure 9:
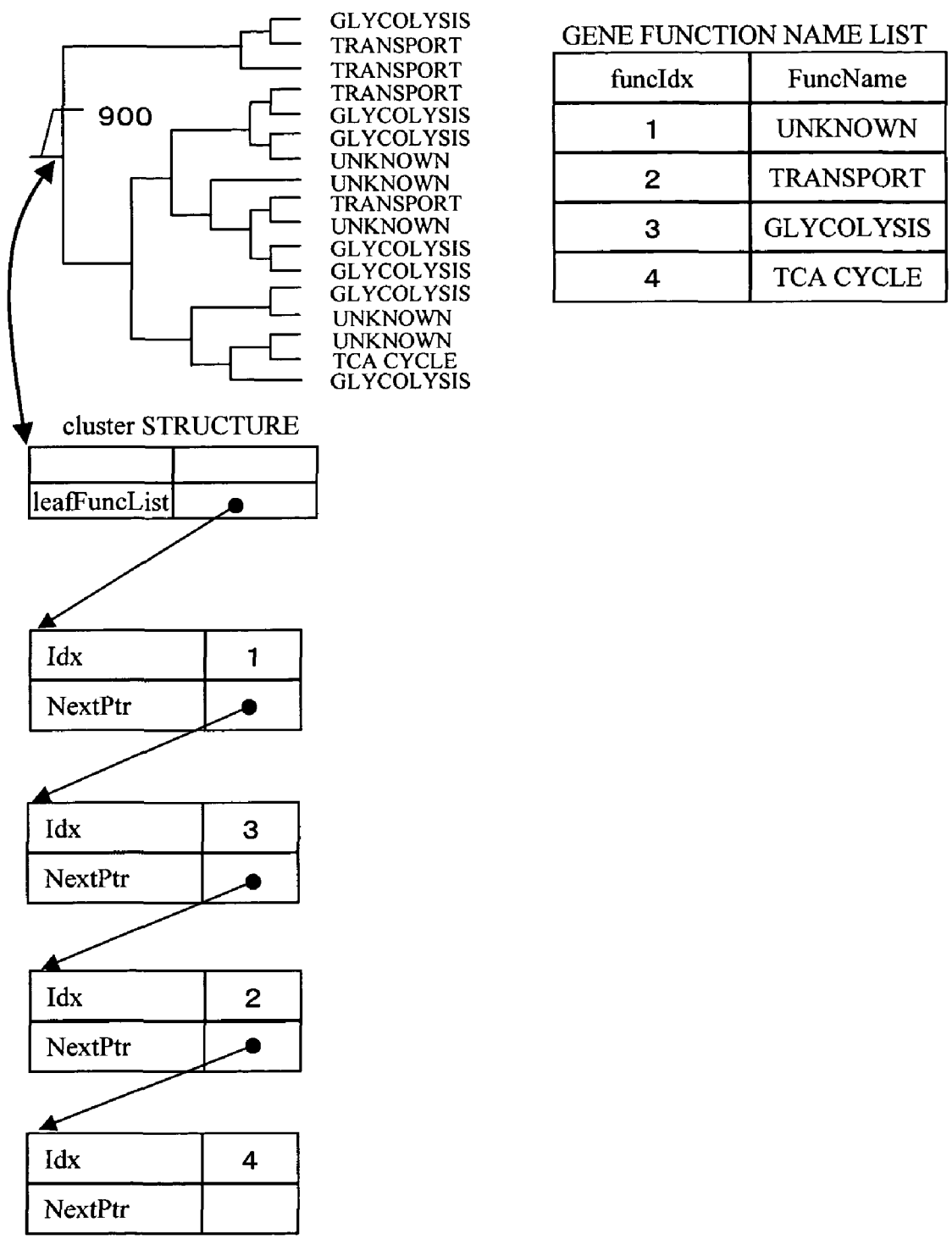
FIG. 9 illustrates an example of storing a function list in the cluster structure.

FIG. 9 illustrates an example of the function list leafFuncList (807) stored in the cluster structure. The function name of each gene is given on the right of the dendrogram. Since the gene of the leaf linked to the node 900 has the functions 'UNKNOWN (funcIdx: 1)', 'TRANSPORT (funcIdx: 2)', 'GLYCOLYSIS (funcIdx: 3)'and 'TCA CYCLE (funcIdx: 4), the leafFuncList of the cluster structure is expressed in the form illustrated in the drawing.

Figure 10:
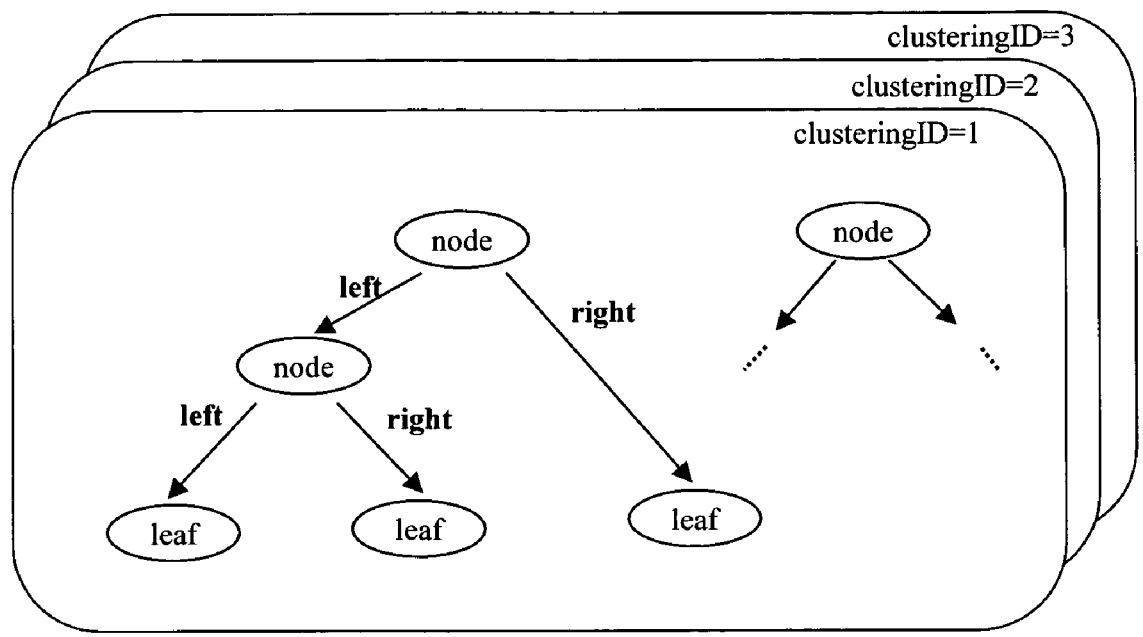
FIG. 10 illustrates an example of generating a cluster tree structure.

FIG. 10 illustrates the data structure generated in the process of cluster analysis. At first only leaf-type cluster structures are prepared, but in the process of cluster analysis they are merged two by two, generating a node-type cluster structure each time to assemble a tree structure. These link structures are managed separately by clusteringID (806). This is because the clusteringID is determined by the method of clustering, and the tree structure changes if the method of clustering does.

Figure 11:
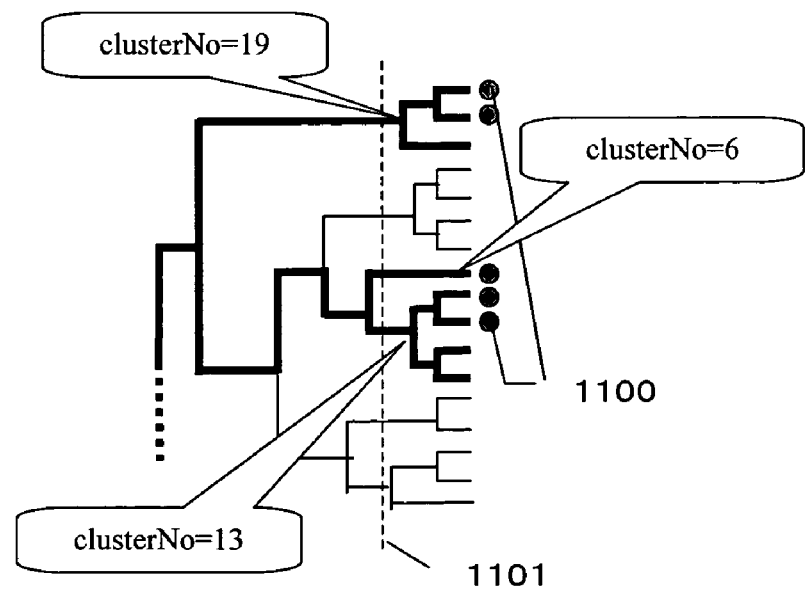
FIG. 11 illustrates an example of storing functionally related genes.

FIG. 11 illustrates an example of a sequence extractNodes[ ] comprising a number en_num of elements for storing functionally related genes. Here are stored the clusterNos of root nodes of subtrees of groups of genes regarded as functionally related genes. For instance, as may be seen from FIG. 11, when genes with a given function are in positions 1100 and the threshold value which determines the similarity of expression is set on the dendrogram in the position shown by the broken line 1101, the clusterNos of nodes severed by the line 1101 determining the threshold value are stored in extractNodes[ ].

Figure 12:
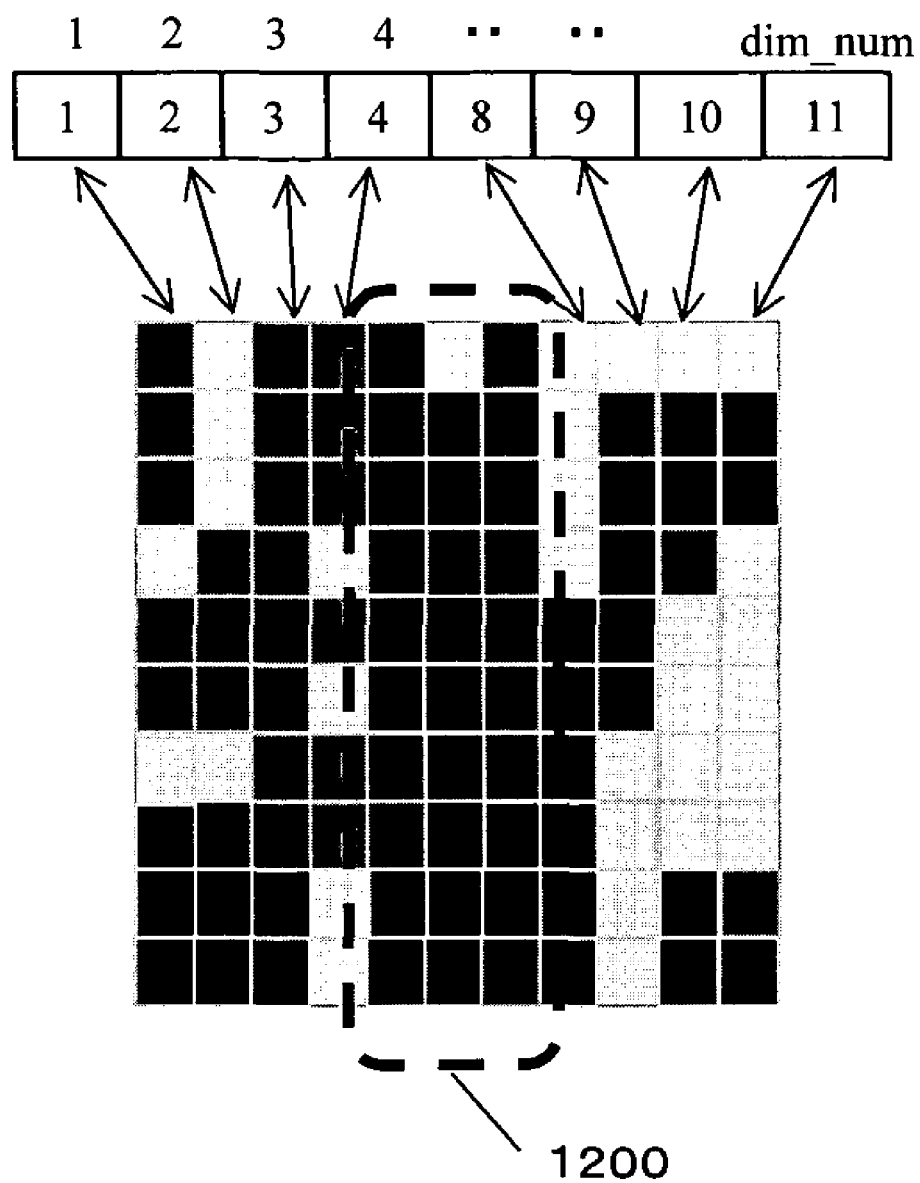
FIG. 12 illustrates an example of the range of data to which clustering is applied.

FIG. 12 illustrates an example of a sequence clustering_dims[ ] comprising a number dim_num of elements for the purpose of storing information on the range of data to which clustering is applied. By the range of data to which clustering is applied is meant the range of suffix number (corresponding to each experiment) when the n-dimensional gene expression vector data is represented by $(x_1, x_2, \ldots, x_n)$. The suffix number corresponding to the object data is stored in the sequence clustering_dims[ ]. For instance, as is shown in FIG. 12, when there are expression data from experiment 1 to experiment 11, and the range from expression data 5 to 7 designated 1200 is excluded from the data to which clustering is applied, the details of the sequence clustering_dims[ ] are as illustrated in the drawing.

Figure 13:
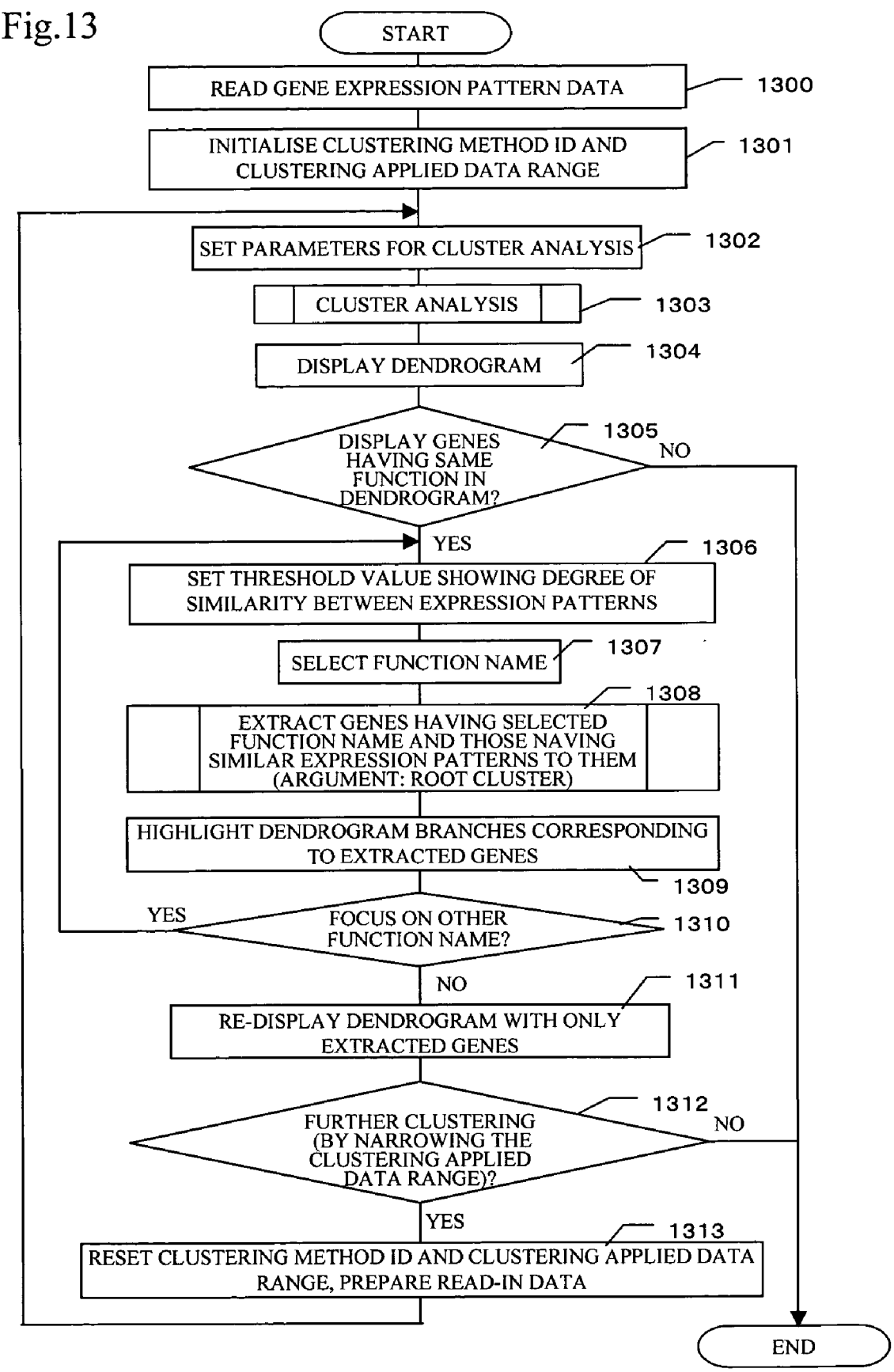
FIG. 13 illustrates a schematic processing flow of the present system.

FIG. 13 illustrates an outline processing flow of the gene cluster method according to the present embodiment.

Firstly, data is read from the gene expression pattern data into the clustering processor 500 (step 1300). Next, 1 is substituted in clustID, which is an ID representing the method of clustering, and 1, 2, 3, . . . , n are substituted in the clustering applied data region clustering_dims[ ], in the order from the initial element, for initialisation. Then m is substituted in gnum, which shows the total number of data for clustering (step 1301). Next, the parameters required for cluster analysis are set (step 1302).

Once the parameters have been initialised and set, cluster analysis is performed (step 1303). This will be described in detail below. Next, the results of the analysis are displayed (1304). Here, the data for display which has previously been collected and calculated (relative distance between clusters) is employed to create a dendrogram and display gene names and functions.

If genes having the same function are to be displayed within the dendrogram at this point, a threshold value is set to show the degree of similarity in expression patterns, and a desired function name is selected (steps 1306, 1307). The threshold value may be set by selecting an appropriate value from the display of clustering results (for instance by moving the mouse right and left along the line 100 of threshold values shown in FIG. 1). If genes having the same function are not to be displayed in step 1305, the process terminates.

Next, genes with the function name selected in step 1307 and those having similar expression patterns to them are extracted (step 1308) by using as an argument the cluster corresponding to the root of the dendrogram that has just been generated. This will be described in detail below. After this process, branches corresponding to the functionally related genes are highlighted as denoted by the thick line in FIG. 1 (step 1309) on the basis of the information about the clusterNo of the subtree root of the extracted genes (functionally related genes) stored in the sequence extractNodes[ ].

If the user wishes to focus on a function name other than that selected at step 1307, he returns to step 1306 and continues the process (step 1310). If not, the dendrogram is re-displayed with only the extracted genes (functionally related genes) as in FIG. 3 (step 1311).

If further clustering is to be performed on the group of functionally related genes, the following processing is performed. Firstly, if it is desired to apply clustering after narrowing the range of data to which clustering is to be applied, the sequence clustering_dims[ ] is renewed. In other words, as may be seen from FIG. 12, the suffix number of the gene expression vector data for clustering is written in clustering_dims[ ]. This suffix number for clustering can also be written by specifying the range on screen with the mouse or otherwise. Then, the clustering method ID clustID and the clustering applied data range are re-set. First, clustID is incremented by 1. The data which is to be read in the clustering process as the clustering applied data range is replaced with the gene group of the functionally related genes extracted at step 1308, and the number of functionally related genes is substituted in gnum, which indicates the total number of data which are to be clustered. Then the program returns to step 1302, and clustering is performed. In step 1312 processing is terminated if no more clustering is applied.

Figure 14:
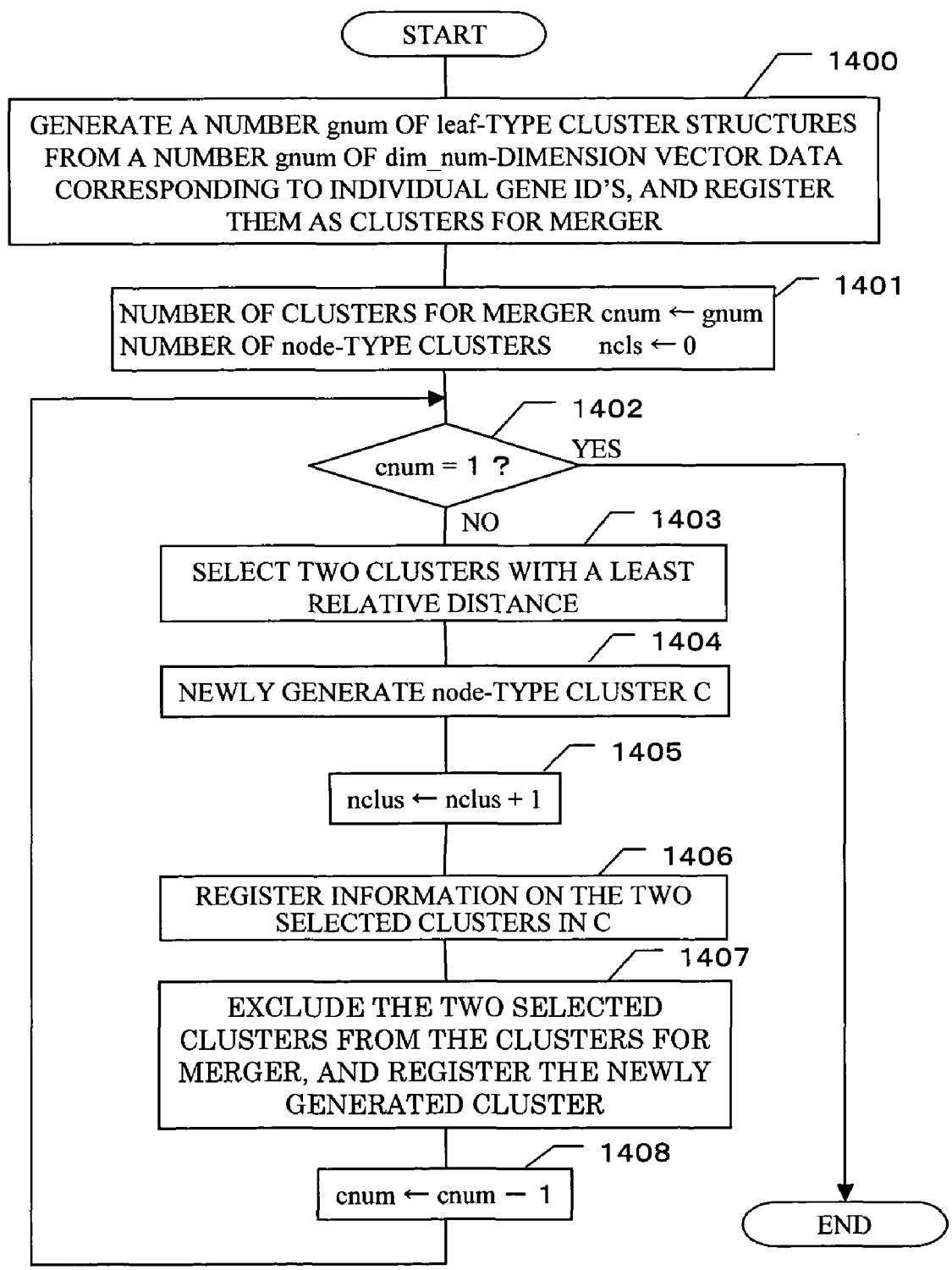
FIG. 14 illustrates a detailed flow of cluster analysis.

FIG. 14 illustrates the detailed flow of the process of cluster analysis in FIG. 13 (step 1303).

Firstly, in the n-dimensional vector (602) formed of expression data corresponding to each gene ID as shown in FIG. 6, the components of that vector whose suffix numbers correspond to the sequence clustering_dims[ ] are taken and new vector data corresponding to the genes is created, where the new vector consists of only taken components. Leaf-type cluster structures corresponding to a number gnum of individual genes are generated and registered as clusters for merger (step 1400). To the clusterNo member values (800)

of the cluster structure are allocated 1, 2, 3, ..., in the order of the gene data that is fed. The gene ID (600) is registered in the geneID member value (805), the clustID is registered in the clusteringID member value (806), and the function of the corresponding genes is registered in leafFuncList member value (807).

Next, the number of clusters to be merged cnum and the number of node-type cluster structures ncls are initialised to gnum and 0, respectively (step 1401). It is then determined to see whether the number of clusters to be merged cnum is equal to 1 (step 1402). If not, the following procedure is repeated until it becomes 1. If it is equal to 1, the process is terminated.

Firstly, the two clusters with a minimum relative distance from the registered clusters which are to be merged are selected (step 1403). Next, a node-type cluster C is newly generated (step 1404), and the number of node-type clusters is incremented (step 1405). The two clusters selected at step 1403 and the distance between them is registered in the left member (802), right member (803) and distance member (804) of the new node-type cluster, and leafFuncLists of the two clusters are added in the leafFuncList member (807). In addition, clustID is registered in the clusteringID member (806), and gnum+nclus is registered in the clusterNo member (800) of C (step 1406).

It is also possible to establish assessment criteria in advance as to which of the two clusters is made the left member and which the right. Finally, these two clusters are excluded from the clusters for merger, the new node-type cluster is registered (step 1407), the value of the number of clusters for merger cnum is decremented (step 1408), and the process is continued from step 1402.

Figure 15:
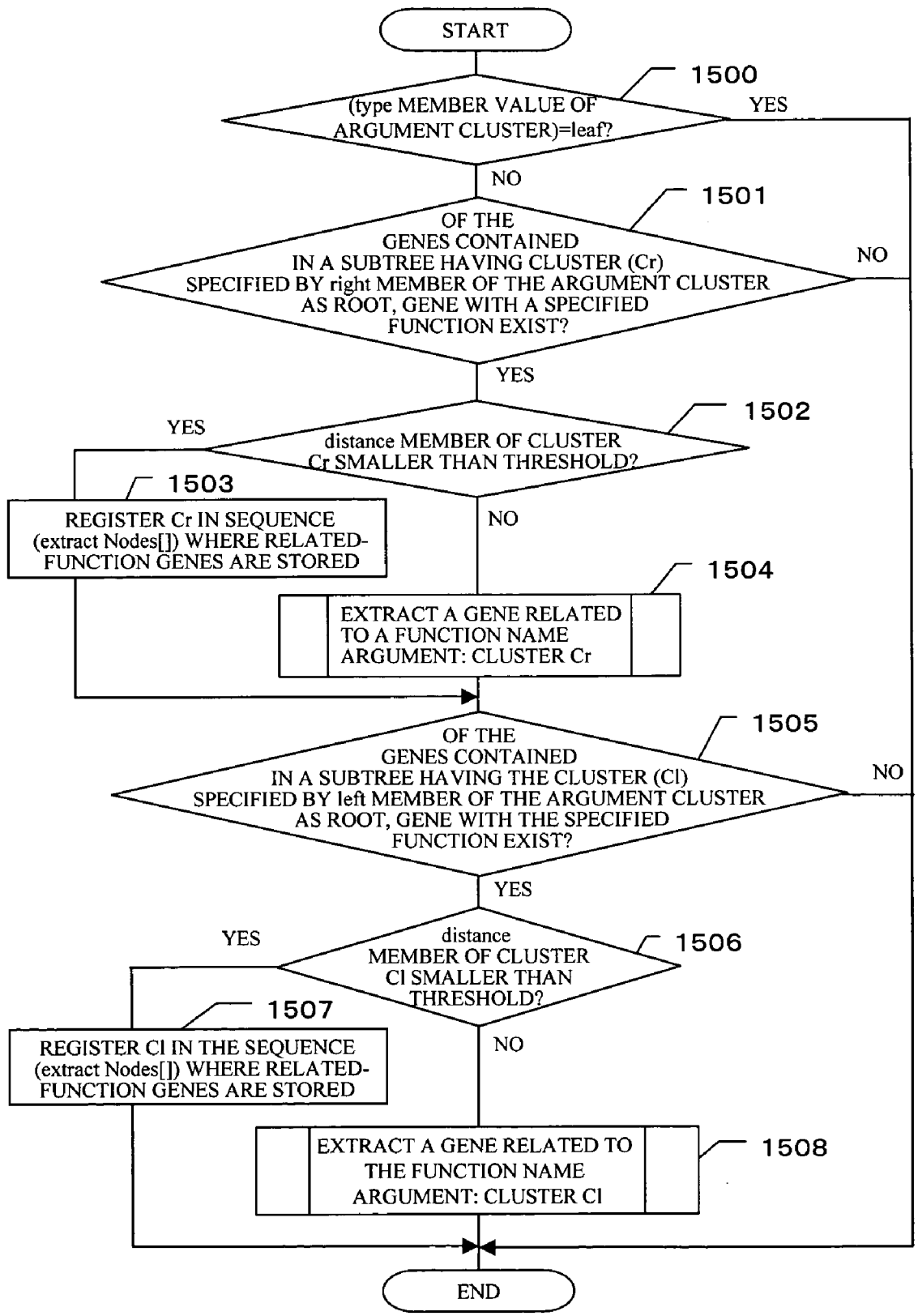
FIG. 15 illustrates the flow of processing to extract a gene related to a function name.

FIG. 15 illustrates the detailed flow of processing to extract the gene related to the function name in FIG. 13 (step 1308).

First, the type member value of the cluster given as the argument is examined. If it is leaf, the process is terminated (step 1500). Next, the right member cluster (Cr) of the cluster given as an argument is examined to see whether or not it contains a function-related gene. In other words, it is examined to see whether or not the function ID of the function name selected at step 1307 in FIG. 13 is included in the list of Cr leafFuncList (807). If it is not included, the process is terminated (step 1501).

If the function corresponding to the cluster Cr is included, it is examined to see whether or not the Cr distance member (804) is smaller than the threshold value determined at step 1306 in FIG. 13 (step 1502). If it is smaller, the Cr clusterNo member value (800) is registered in the sequence (extractNodes[ ]) where the function-related genes are stored (step 1503). If the distance member is greater than the threshold value at step 1502, the genes related to the function name are again extracted with the cluster Cr as the argument (process illustrated in FIG. 15).

The same process is performed on the left member cluster of the cluster given as the argument, and the process is terminated (steps 1505–1508).

In this manner it is possible to display and analyse the results of cluster analysis as illustrated in FIGS. 1–4.

Second Embodiment

There now follows a description of an embodiment aimed at achieving the second object of the present invention. The system of the present embodiment is configured in the same manner as in FIG. 5. Moreover, the gene data and gene function name list used are the same as those illustrated in FIGS. 7 and 8 and described in relation to the first embodiment.

The present embodiment calculates how many functions are there in the genes belonging to a subtree, and determines the proportion of each function in the subtree. If a proportion in the subtree exceeds a previously determined threshold value, it is regarded as a function cluster and extracted. In order to prevent a single gene from being regarded as a function cluster by itself, at least the number of genes contained in a cluster is determined in advance as a threshold value.

Figure 16:
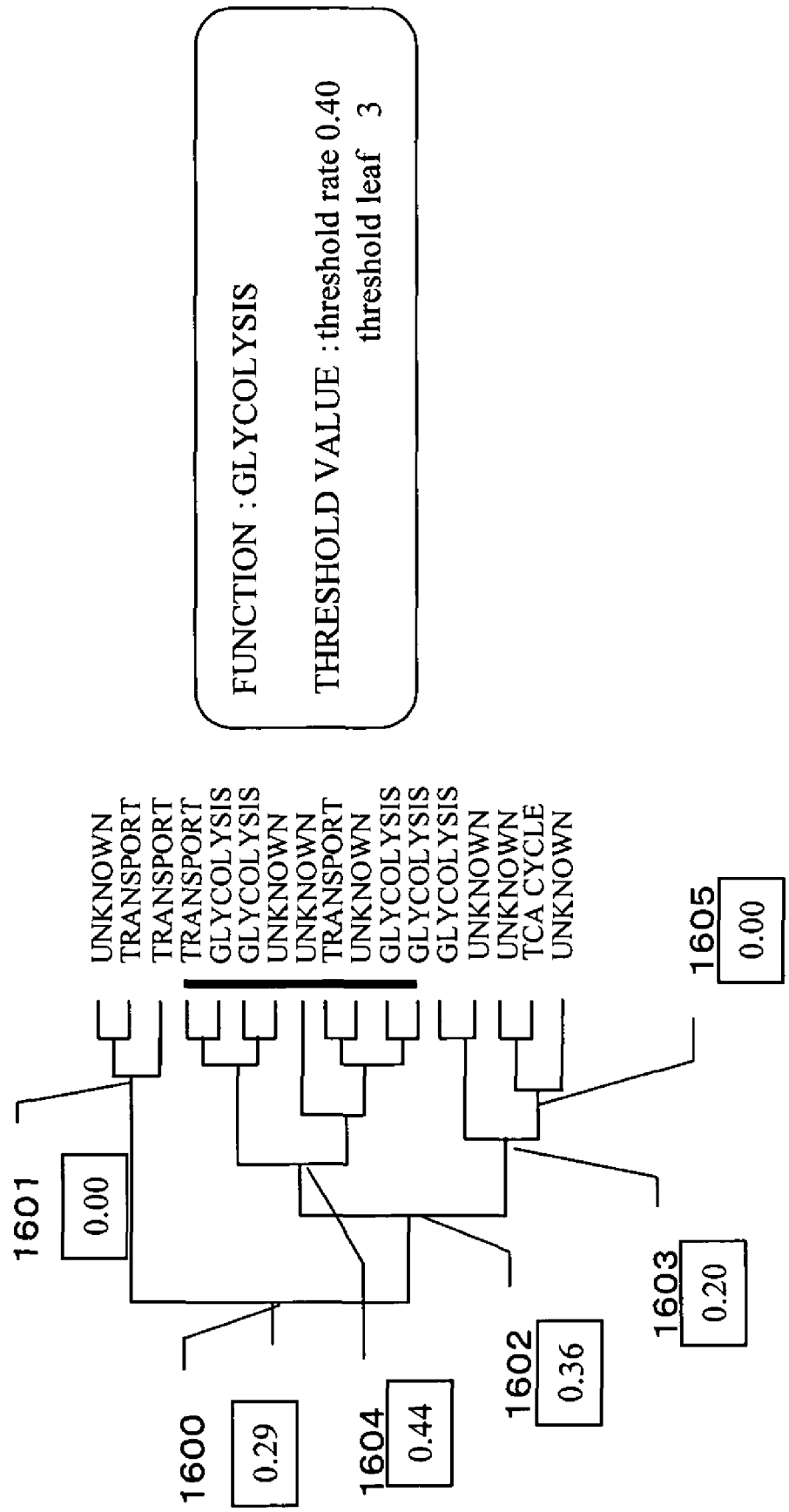
FIG. 16 illustrates a model of cluster extraction processing.

FIG. 16 illustrates a model of cluster extraction processing. The process illustrated is that of searching for function clusters relating to genes with GLYCOLYSIS as their function. In this example, as shown on the right of FIG. 16, the minimum proportion having the function of GLYCOLYSIS in the subtree is set at 0.40, and clusters containing at least three genes are to be selected.

In the case of the example illustrated in FIG. 16, it can be seen that, as to the root node 1600 of the dendrogram, the number of genes having the function GLYCOLYSIS is five, so that the proportion of such genes to the total number of genes in the subtree (17) is 5/17=0.29. This is smaller than the minimum proportion (0.40) set as the threshold value, and therefore the subtree of node 1600 is not regarded as a function cluster related to the function GLYCOLYSIS.

Next, the proportion of genes having the function GLYCOLYSIS is calculated in the same manner for the two sub-nodes 1601 and 1602 belonging to the node 1600. When these nodes are considered as roots the proportions are 0.00 and 0.36, respectively, so that the nodes 1601 and 1602 are not regarded as function clusters in relation to the function GLYCOLYSIS. As far as node 1601 is concerned, if the sub-nodes to the left and right are regarded as roots of a subtree, the numbers of genes are two and one, respectively, which does not fulfil the condition of selecting a cluster with at least three genes. Thus the search is not continued.

The proportion of genes having the function GLYCOLYSIS is calculated in the same manner for the sub-nodes 1603 and 1604 on the left and right of the node 1602. In node 1604 the proportion of genes having the function GLYCOLYSIS is 0.44, which is higher than the proportion determined according to the threshold value. As a result, this is regarded as a function cluster. On the other hand, the node 1603 and its sub-node 1605 have proportions of GLYCOLYSIS lower than the threshold value, and are therefore not regarded as constituting function clusters. The function clusters are determined in this manner.

Figure 17:
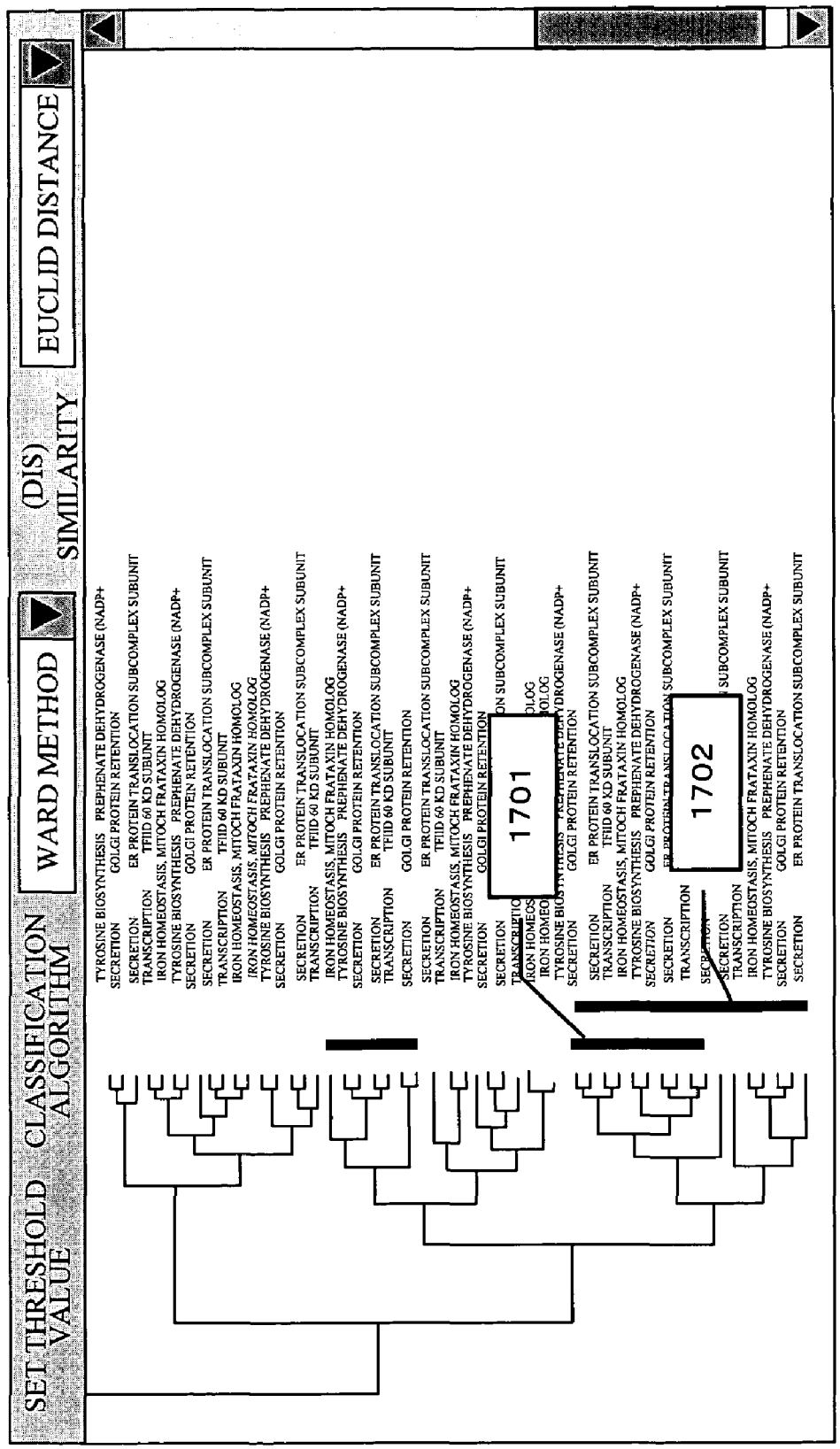
FIG. 17 illustrates an example of a screen display in accordance with the present invention (screen displaying a dendrogram and function cluster)

FIG. 17 is an example of screen display according to the present embodiment.

Function clusters are shown by drawing vertical bars beside the dendrogram. There are cases as with 1701, 1702 where the bars overlap. This is because the genes have a plurality of functions, and the function cluster parts are displayed for both functions. The function clusters only need to be highlighted in such a manner as to be distinguishable from other parts, and there are other methods of achieving this apart from drawing bars. Examples include changing the colour of the clusters and surrounding them with a frame.

Figure 18:
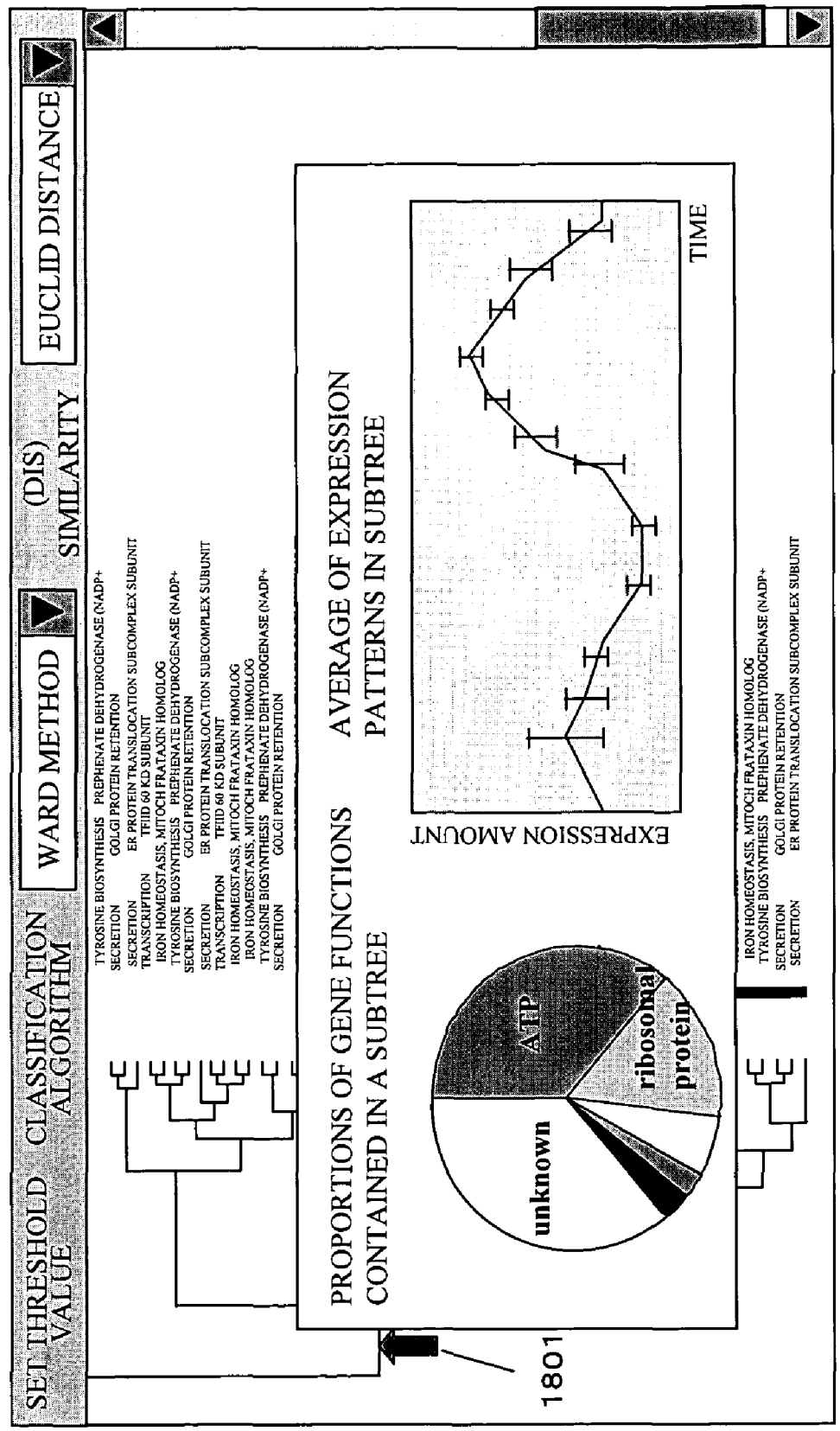
FIG. 18 illustrates an example of a screen display in accordance with the present invention (screen displaying subtree data)

FIG. 18 is another example of a screen display in accordance with the present embodiment. In this example, selecting a branch of a subtree with the mouse causes the proportions of gene functions contained there to be displayed on a circle graph. Further, the average and statistical variance of expression patterns of individual genes belonging to the subtree selected with the pointer 1801 are calculated and displayed on the graph, where the horizontal axis shows the experiment case, for example time. Adopting this method of display particularly in relation to function clusters is useful for inferring the function of genes of which the function is not yet known, and also makes it possible to discover expression patterns specific to functions.

Figure 19:
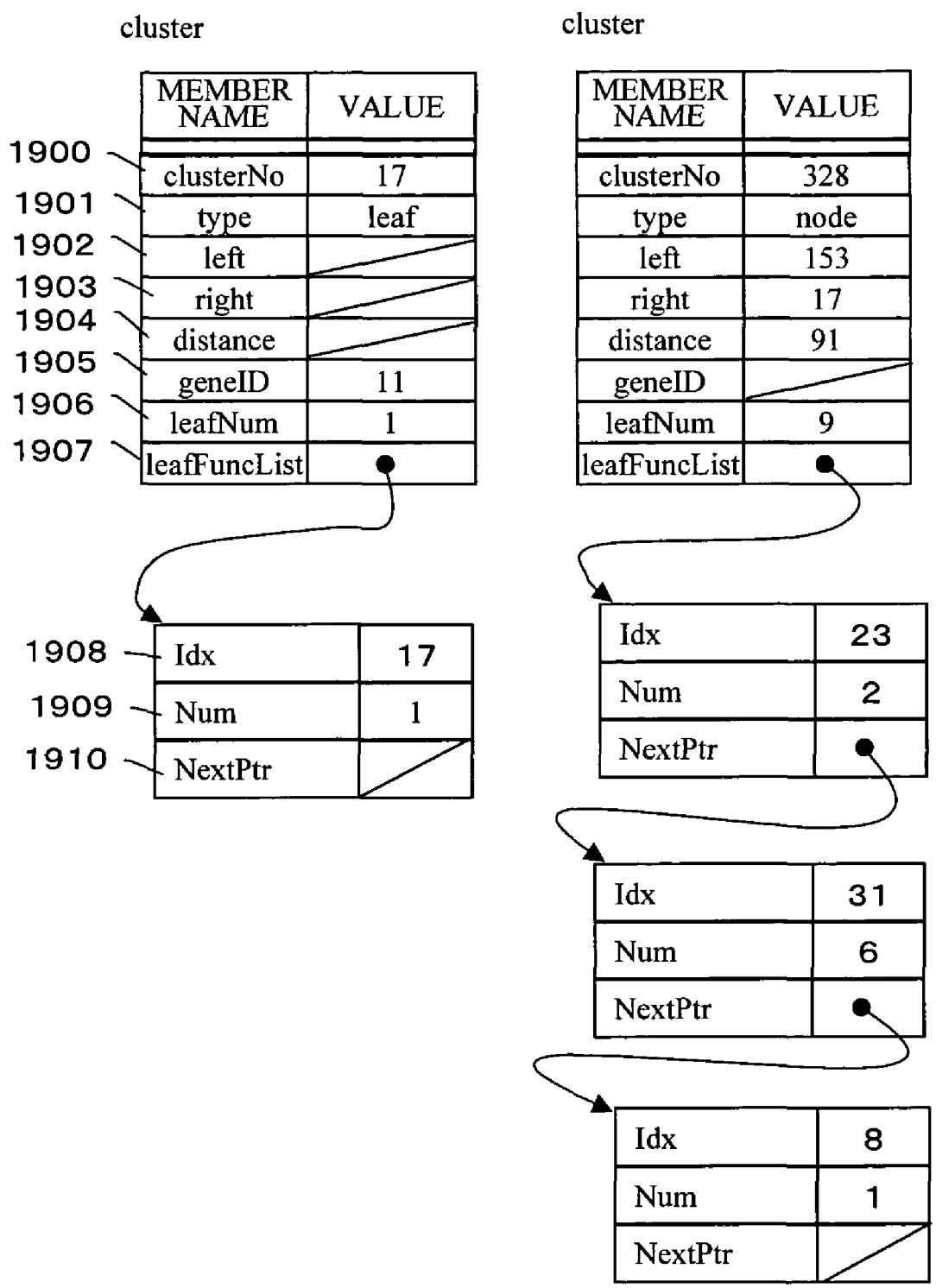
FIG. 19 illustrates an example of a cluster structure.

FIG. 19 illustrates an example of cluster structure used in the clustering process in the present embodiment. Each cluster structure corresponds to a node or leaf on the dendrogram. In order to identify each cluster, a unique clusterNo (1900) is allocated to each cluster structure. There are two types of cluster structure. These correspond to clusters representing leaves and those representing intermediate nodes, and are divided by the type member (1901) value respectively into leaf (left) and node (right).

The node-type cluster structures are generated successively in the process of merging during clustering, and the two clusters prior to merging can be traced from the left (1902) value and right (1903) value. Moreover, the distance ((dis)similarity) between them is retained as the distance (1904) value. A unique clusterNo (1900) representing the cluster is entered in left and right.

The leaf-type cluster structures each correspond to one gene, and data on gene information structures can be referred to by storing the gene ID (600) in geneID (1905). In the case of node-type cluster structures, the number of leaf-type structures belonging to the cluster is stored in leafnum (1906), while the functions of genes corresponding to the leaf-type structures belonging to the cluster are stored by type in leafFuncList (1907) in a list structure. In the case of leaf-type cluster structures, 1 is stored in leafnum (1906), while the function of the corresponding gene is stored in leafFuncList (1907) in a list structure.

One list comprises idx (1908) for storing function ID, Num (1909) showing the number of times that function appears in the subtree, and NextPtr (1910) for storing the pointer to the next list. The function ID stored in idx is the index of funcList in the gene function name list.

Where a gene has a plurality of functions, 1 is divided by the number of functions, and the number of times Num (1909) a function appears is represented as an equal fraction of 1, or alternatively each of the plurality of functions may be represented by 1. For instance, if a gene has the functions 'TRANSPORT', TCA CYCLE' and 'GLYCOLYSIS', and the number of times a function appears is represented as n equal fraction of 1, funcList will comprise three lists, and Num will be 0.33 in each of them.

Figure 20:
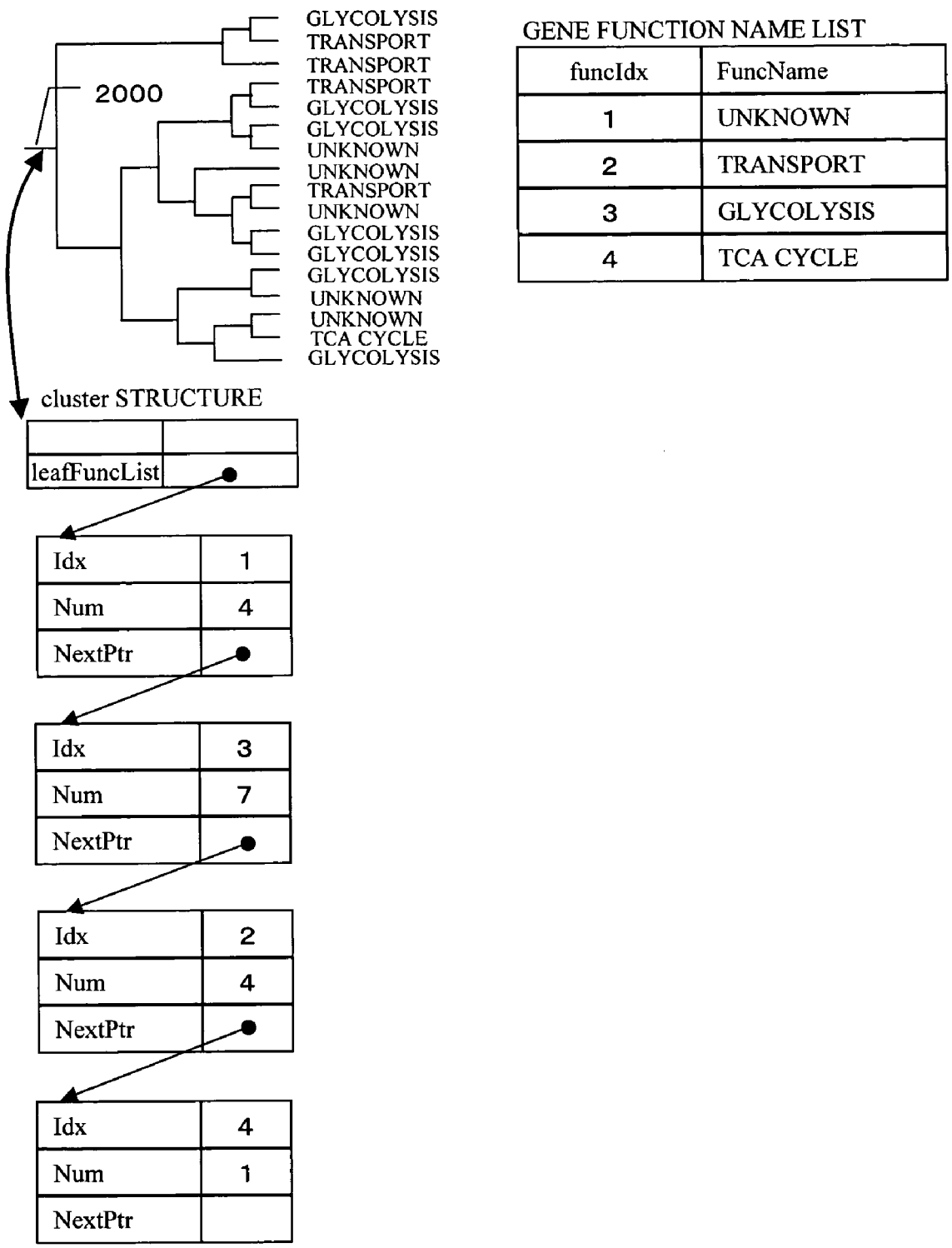
FIG. 20 illustrates an example of storing a function list in a cluster structure.

FIG. 20 illustrates an example of storing a function list leafFuncList (1907) in the cluster structure illustrated in FIG. 19. The function name of each gene is shown on the right of the dendrogram. Of the genes joined to node 2000, four have the function "UNKNOWN (funcIdx: 1)", four "TRANSPORT (funcIdx: 2)", seven "GLYCOLYSIS (funcIdx: 3)", and one "TCA CYCLE (funcIdx: 4)", so that the leafFuncList of the cluster structure is expressed in the form shown in the diagram.

Figures 21, 22:
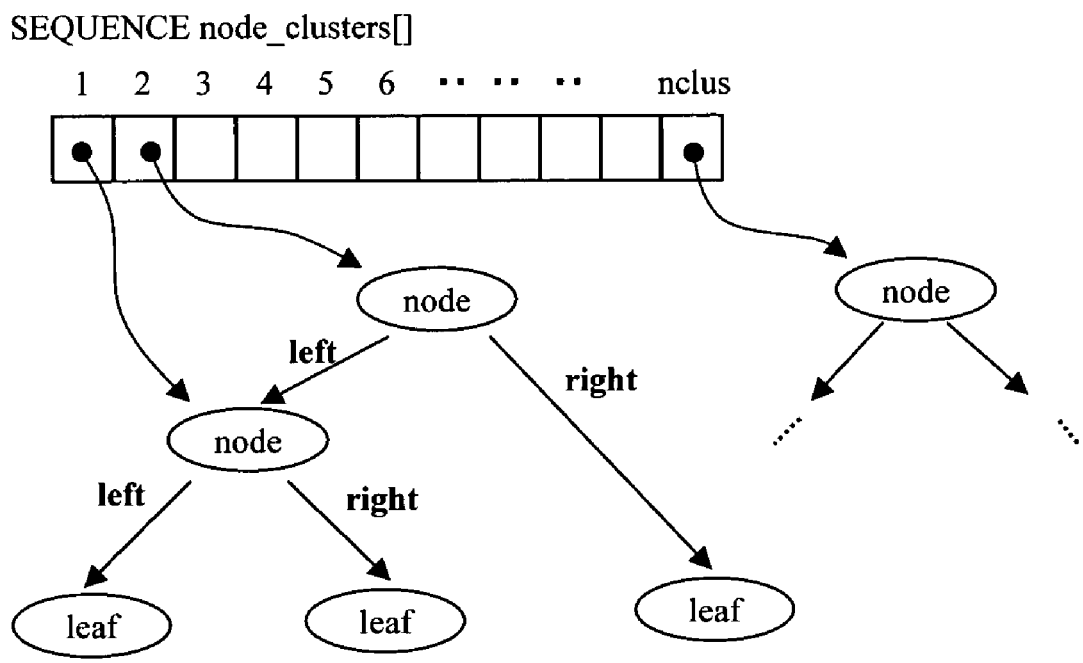
FIG. 21 illustrates an example of generating cluster tree structures.
FIG. 22 illustrates an example of a structure for storing the results.

FIG. 21 illustrates data structure generated in the process of cluster analysis. At first only leaf type structures are prepared, but in the process of cluster analysis they are merged two by two, generating a node-type cluster structure each time to assemble a tree structure. The node-type clusters create pointers in the order in which they are generated so that they can be traced from the sequence node_clusters[ ]. The variable nclus retains the total number of node-type cluster structures created.

FIG. 22 illustrates the sequence results[i] (i=1, 2, 3, . . . , func_num) of the structure for storing results. The index i of results[i] corresponds to each function ID (funcIdx). In other words, one results[ ] element is allocated to each function. The structure results[ ] members comprise threshold value and extracted results. The threshold value comprises threshold rate (2200), that is the proportion of a function which should be contained in one subtree, and threshold leaf (2201), that is the minimum number of leaf-type clusters which should be contained in the subtree. The extraction result is represented by result (2202). Here the clusterNo of intermediate nodes (type clusters) representing function clusters is stored.

The threshold value can be set by the user by operating the keyboard or mouse. In particular, as to the threshold rate (2200), a certain value may be given to individual functions uniformly. If the proportion of any one function is relatively large from the beginning, the proportions may be varied accordingly. Several other ways may be contemplated.

Figure 23:
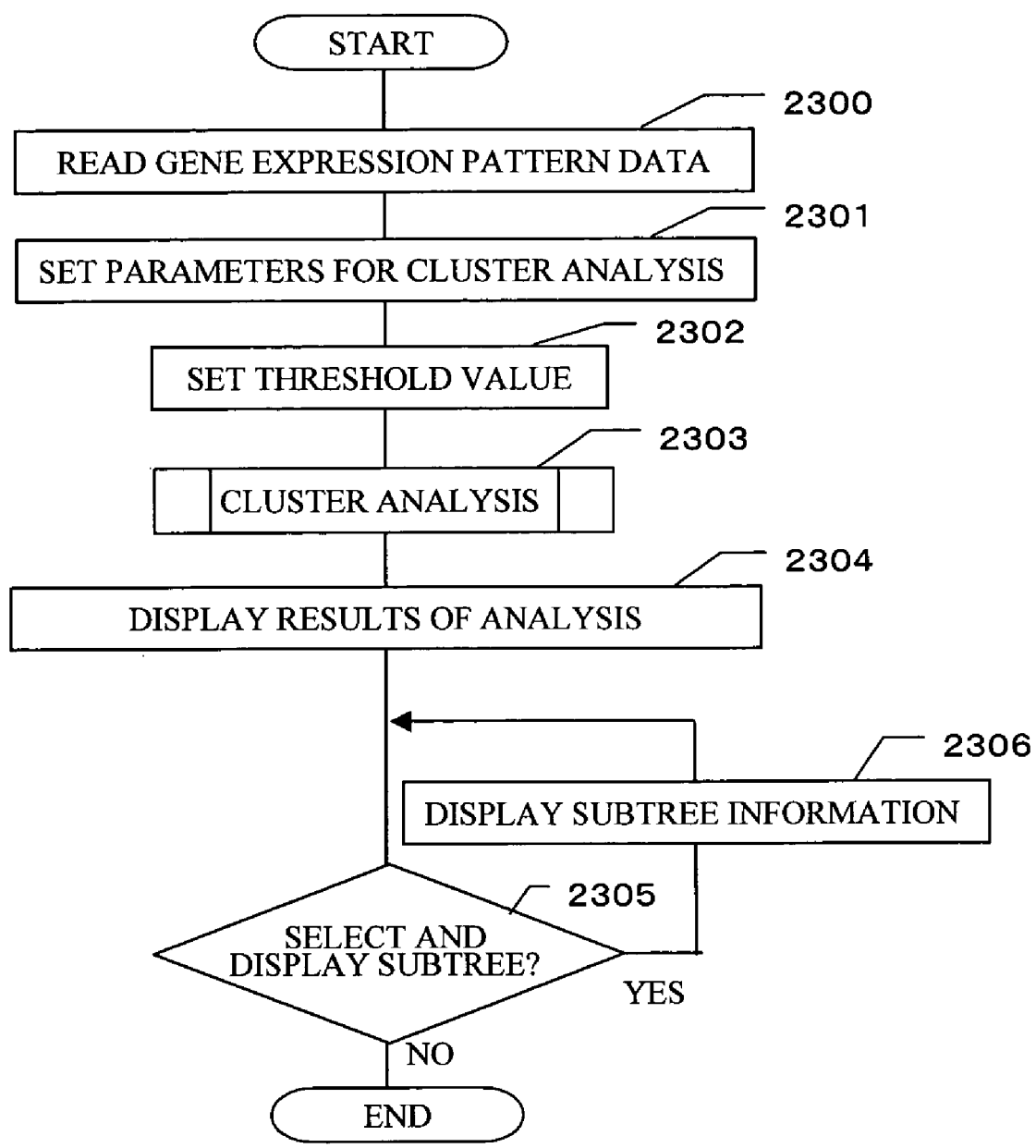
FIG. 23 illustrates a schematic flow of the present system.

FIG. 23 illustrates the outline process flow of the gene clustering method according to the present embodiment.

Firstly, data is read from the gene expression pattern data into the clustering processor 500 (step 2300). Next, the various parameters and threshold values required for cluster analysis are set (steps 2301, 2302). Once the parameters have been set, cluster analysis is performed (step 2303). During the process of cluster analysis the information required for function cluster display according to the present invention is collected and the data for use in display are calculated. This will be described in detail below.

Next, the results of the analysis are displayed (2304). The data for display which has been collected and calculated (relative distance between clusters) is used to create a dendrogram, and gene names and functions are displayed. The leaf nodes (leaf-type cluster structures) linked to the intermediate nodes (node-type cluster structures) specified by result members in the results[ ] sequence are indicated by bars such as designated 1701, 1702 in FIG. 17.

If a subtree is to be selected and displayed at this point, the distribution of gene functions of the leaf nodes included in a selected subtree are displayed as shown in FIG. 18, and an average expression pattern of the genes is displayed (steps 2305, 2306). For display, since the distribution of functions is stored in the leafFuncList (1907) of the intermediate nodes (node-type clusters) corresponding to the subtree selected, function distribution may be created on the basis of the stored distribution, while the average and variance of expression pattern may be created on the basis of the expression data (602) in the gene data sequence gene[ ] by tracing back to the leaf cluster. If no subtree is selected, the process terminates.

Figure 24:
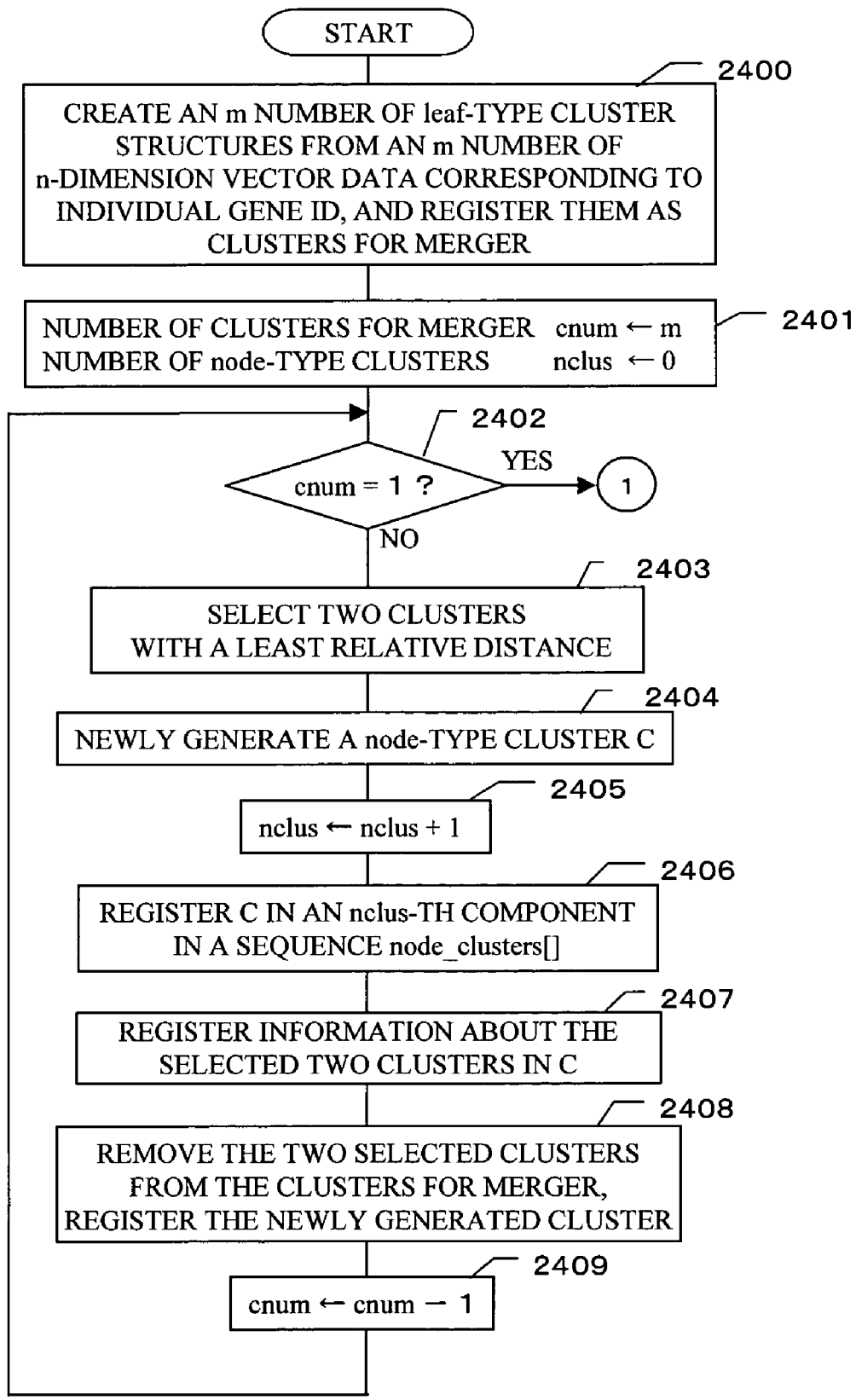
FIG. 24 illustrates a detailed flow of cluster analysis (cluster tree generation)

FIG. 24 illustrates the detailed flow of the process of cluster analysis (step 2303) in FIG. 23, and relates to the process of generating a cluster tree as the first stage.

Firstly, an m number of n-dimensional vector data (602) corresponding to each gene ID illustrated in FIG. 6 are taken as an m number of leaf-type cluster structures and registered as clusters for merger (step 2400). The clusterNo is added to the gene[ ] index, the geneID (1905) is added to GENE ID (600), leafnum (1906) is made 1, and corresponding gene functions are added to leafFuncList (1907).

Next, the value cnum of the number of clusters for merger and the number ncls of node-type cluster structures so far created are initialised to m and 0, respectively (step 2401). It is assessed to see whether or not the number of clusters for merger is equal to 1 (step 2402). If it is not equal, the process outlined below is repeated until it becomes 1.

Firstly, two clusters with a least relative distance from the registered clusters which are to be merged are selected (step 2403). Next, a new node-type cluster C is generated (step 2404), and the number of node-type clusters is incremented (step 2405). The new node-type cluster is registered in an nclus-th component of the sequence node-clusters[ ] (step 2406). The two clusters selected at step 2403 and the distance between them are registered in the left member (1902), right member (1903) and distance member (1904) of the new node-type cluster, respectively, the sum of the two clusters' leafnum is registered in the leafnum member (1906), and the sum of the two clusters' leafFuncList is registered in the leafFuncList member (1907). m+nclus is registered in the clusterNo member (step 2407).

Here, it is possible to establish assessment criteria in advance as to which of the two clusters should be regarded as the left member and which as the right member. Finally, these two clusters are excluded from those destined for merger, a new node-type cluster is registered (step 2408), and the value of the cluster number cnum destined for merger is decremented (step 2409). If the value of cnum in the assessment at step 2402 is equal to 1, the procedure goes to the flow illustrated in FIG. 25.

Figure 25:
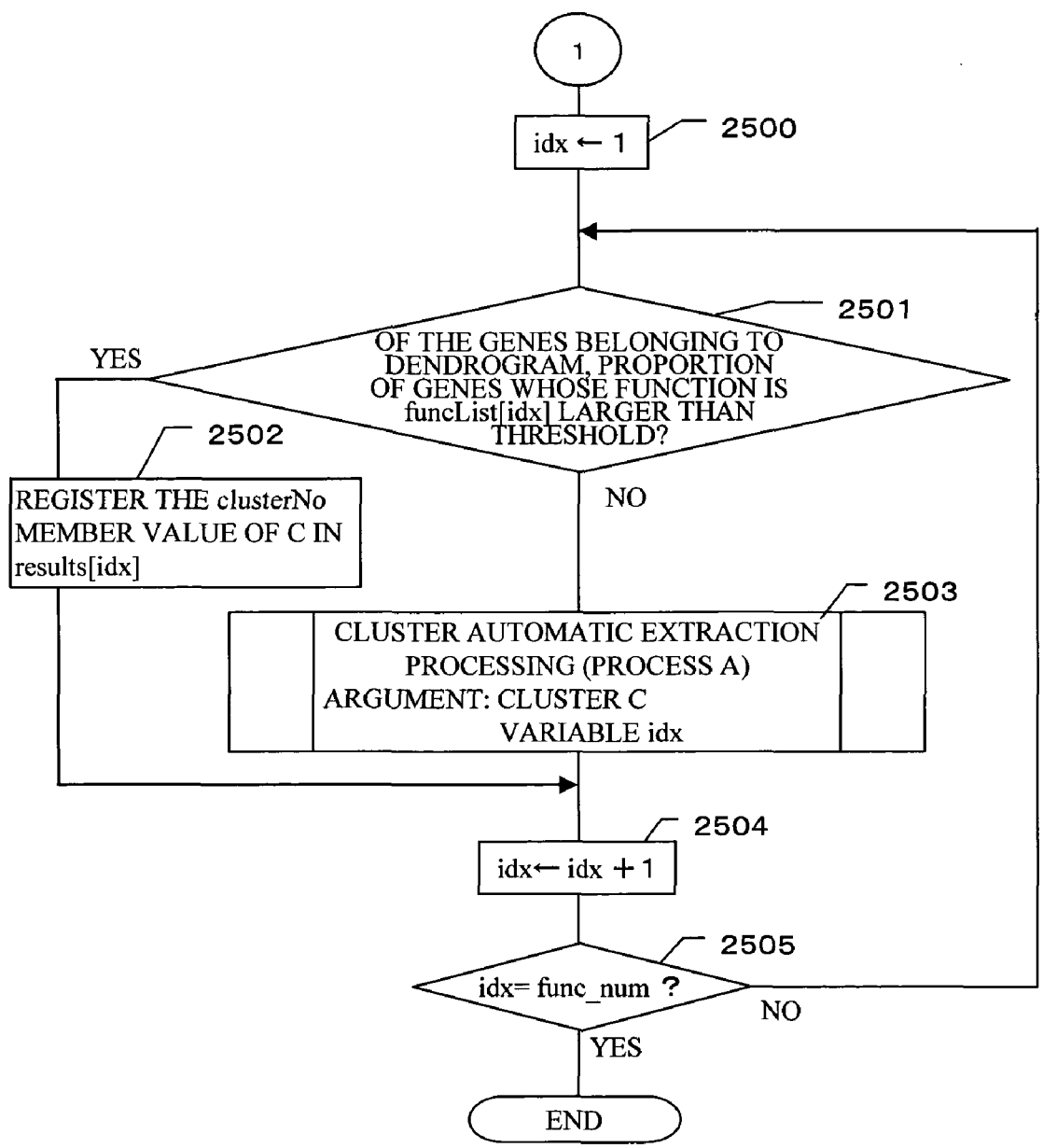
FIG. 25 illustrates a detailed flow of cluster analysis (automatic cluster extraction)

FIG. 25 illustrates the detailed flow of cluster analysis (step 2303) in FIG. 23, the flow relating to automatic extraction of function clusters at a second processing stage.

Firstly, idx which represents the index of the gene function name list is initialised to 1 (step 2500). In the processes hitherto C has been made into a root node of the dendrogram. All the genes belonging to the dendrogram are assessed to see whether or not the proportion of those whose function is funcList[idx] is greater than the proportion of functions which should be contained in the subtree (threshold rate member value of result[idx]) (step 2501). If it is greater, the clusterNo member value of C is registered in the result member value of the results[idx] (step 2502). If it is smaller, cluster extraction (process A) is performed with C and idx as arguments (step 2503). Process A will be described in detail below.

Then idx is incremented by 1. steps 2501–2504 are performed until idx becomes func_num, i.e., for all the functions in the gene function name list (steps 2504, 2505). The whole process terminates when idx becomes func_num.

Figure 26:
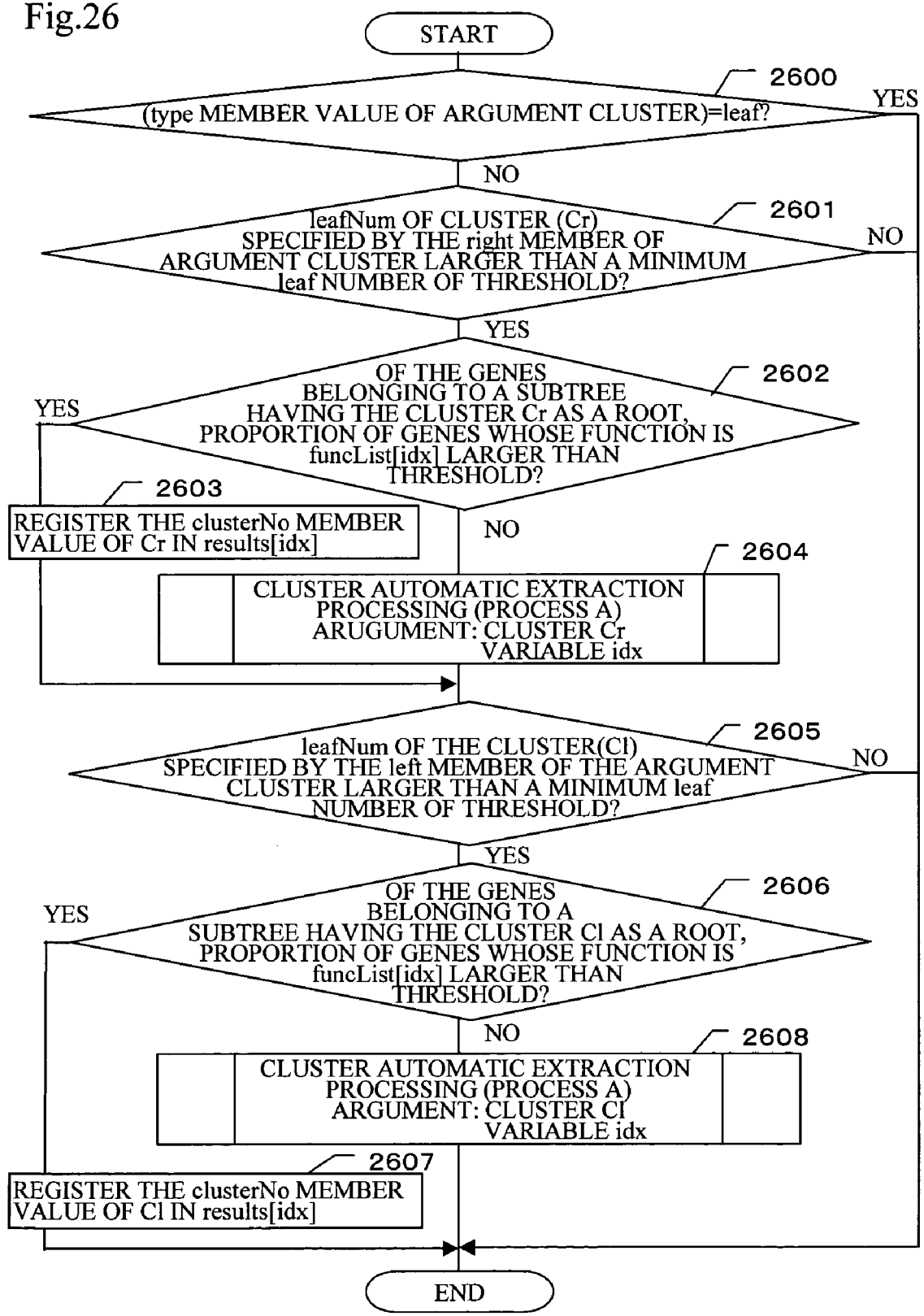
FIG. 26 illustrates a detailed flow of cluster extraction processing (process A)
Figure 27:
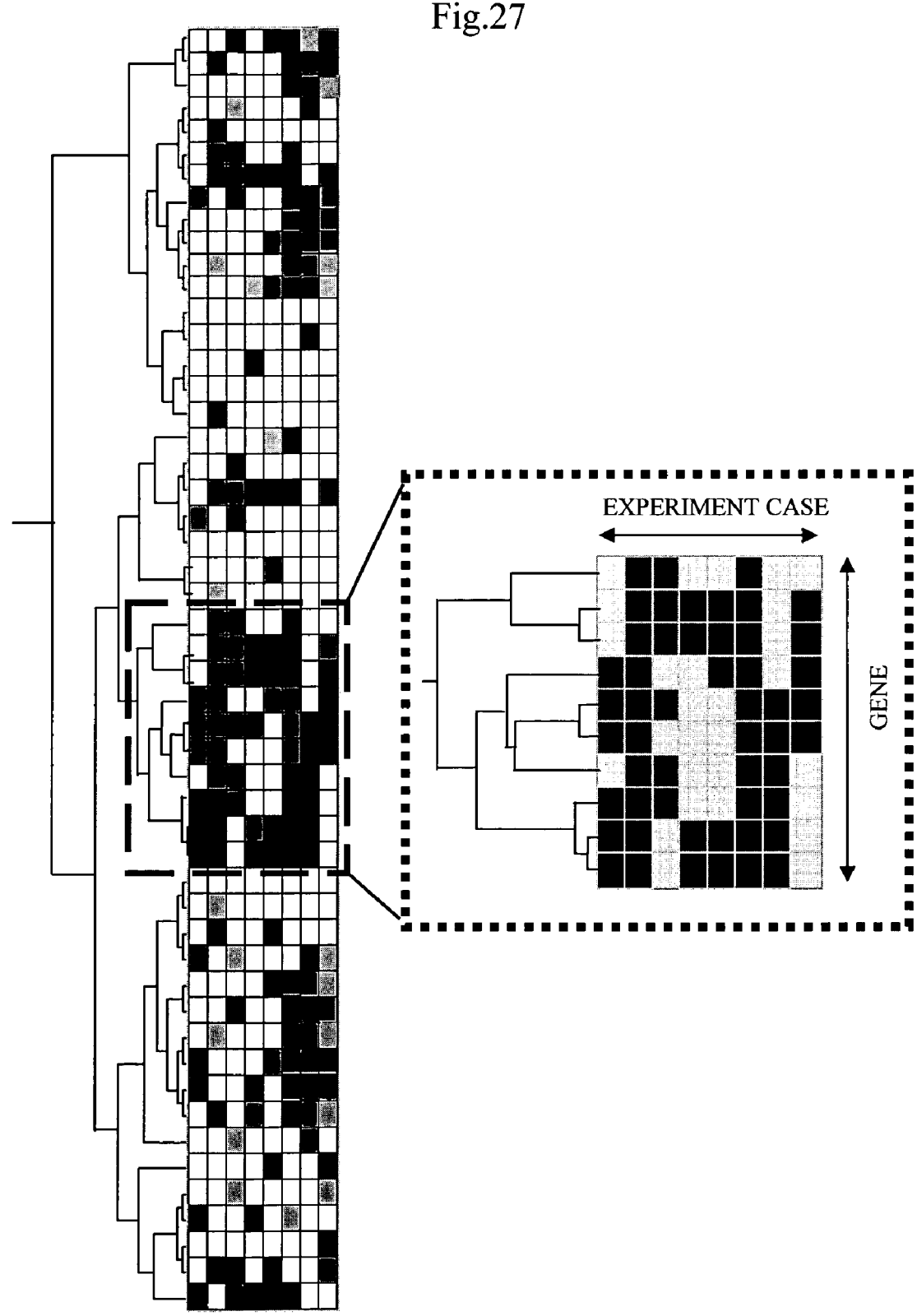
FIG. 27 illustrates an example of how the results of standard cluster analysis are displayed.
Figure 28:
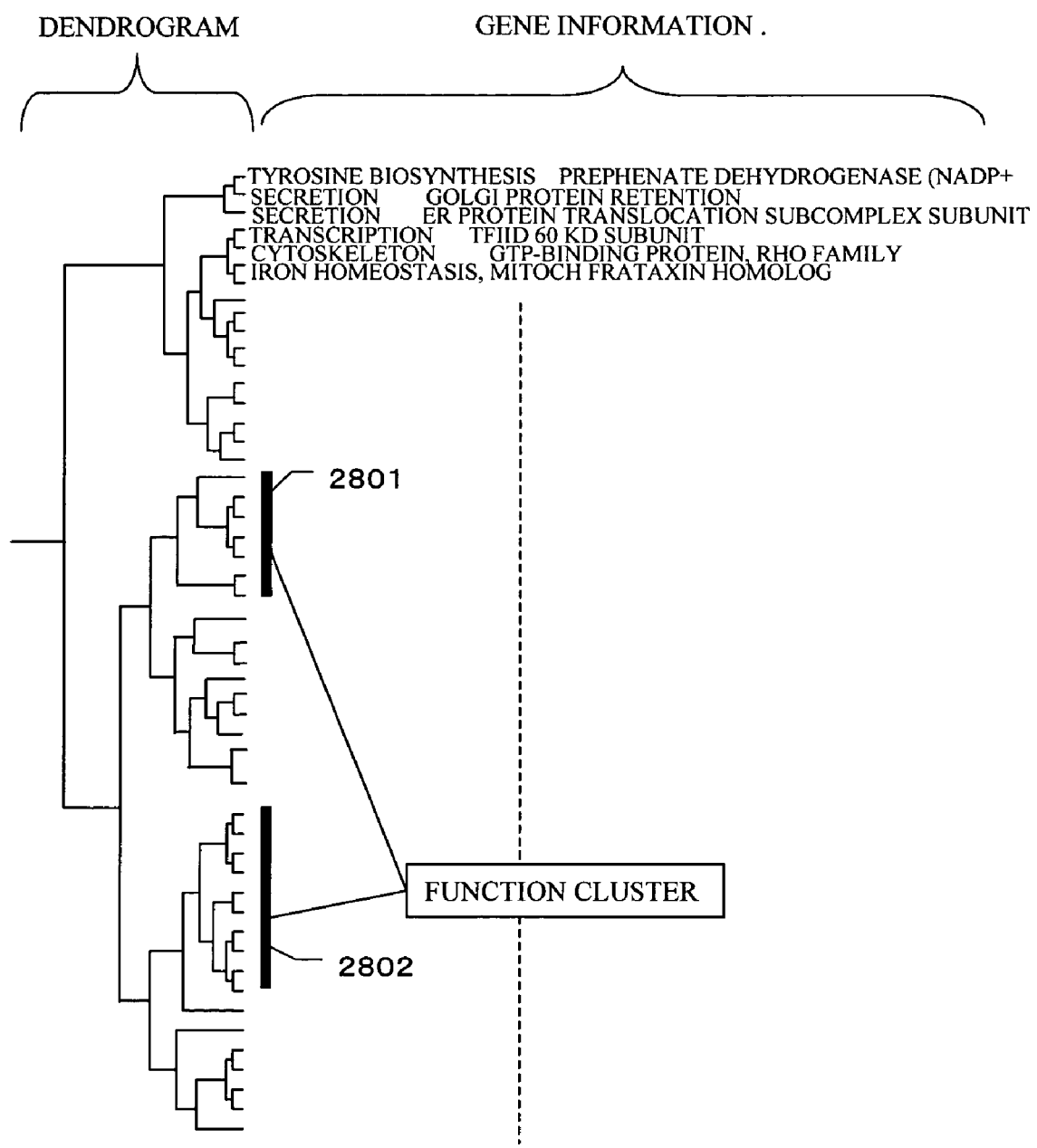
FIG. 28 illustrates an example of how the results of standard cluster analysis are displayed.

FIG. 26 illustrates the detailed flow of process A (step 2503) in FIG. 25.

First, the type member value of the cluster given as the arguments is examined. If it is a leaf, the process is terminated (step 2600). Next, the right member cluster of the cluster given as the argument is examined to see whether or not it is a function cluster. First, the member value leafNum of the cluster (Cr) shown by the right member of the argument cluster is examined (step 2601) to see if it is greater than the minimum leaf number of the threshold value, i.e., the threshold leaf (2201) member value of result [idx]. If it is smaller, process A terminates.

If it is greater, the subtree with cluster Cr as the root is examined to see whether, of the genes belonging to that subtree, the proportion of the genes with the function funcList[idx] is greater than the threshold value. In other words, the number of functions corresponding to funcList [idx] of the leafFuncList (1907) of Cr is examined to see whether the value thereof divided by the leafnum (1906) is greater than the threshold rate member value (2200) of result[idx] (step 2602)), If it is greater, the clusterNo member value of C is registered in the result member value of results[idx] (step 2603). If it is smaller, cluster extraction processing (process A) is performed with Cr and idx as arguments (step 2604).

Next, it is examined to see whether the left member cluster of the cluster given as the argument is a function cluster in the same manner as in steps 2601–2604. Process A terminates when all the above processing is over.

By means of the above processing it is possible to display the results of cluster analysis as illustrated in FIGS. 17 and 18.

INDUSTRIAL APPLICATION

As has been explained above, by highlighting a gene group having the same function and genes having expression patterns similar to the genes in that group on the basis of the results of clustering, the present invention makes it possible for one to comprehend where on a whole dendrogram those genes are located. Moreover, by extracting these genes and comparing their expression patterns, expression patterns specific to individual functions can be found. Furthermore, by performing a different method of clustering for cluster analysis on the extracted genes, for example, estimation of the function of genes with hitherto unknown functions and estimation about whether or not they have other functions can be facilitated.

Further, the present invention allows a group of genes with similar inter-gene expression patterns and with a number of the same known functions to be extracted automatically. By selecting a subtree of a function cluster and displaying it in detail, what gene functions are gathered there can be known, which facilitates the estimation of functions of genes having hitherto unknown functions. The invention also makes it possible for one to understand what patterns are specific to individual functions.

The invention claimed is:

1. A method of displaying gene data, comprising steps of:
displaying a dendrogram obtained by performing cluster analysis on a plurality of gene expression patterns;
specifying a function of a gene to be cluster-extracted, and a condition for function cluster extraction; and
highlighting in the dendrogram a gene function cluster which satisfies the condition in units of subtrees in the dendrogram,
wherein the specified function is transport, glycolysis, or TCA cycle, and
the condition for extracting function clusters comprises a minimum ratio of a number of genes having the specified function within the subtree to a total number of genes within the subtree, and a minimum number of genes contained in one function cluster that has the specified function.

* * * * *